US010421801B2

(12) United States Patent
Chakrabarty et al.

(10) Patent No.: US 10,421,801 B2
(45) Date of Patent: Sep. 24, 2019

(54) CYTOTOXIC FACTORS FOR MODULATING CELL DEATH

(71) Applicant: The Board of Trustees of the University of Illinois, Urbana, IL (US)

(72) Inventors: Ananda M Chakrabarty, Villa Park, IL (US); Tapas K Das Gupta, River Forest, IL (US); Vasu Punj, Chicago, IL (US); Olga Zaborina, Brookfield, IL (US); Yoshinori Hiraoka, Chicago, IL (US); Tohru Yamada, Oak Park, IL (US)

( * ) Notice: Subject to any disclaimer, the term of this patent is extended or adjusted under 35 U.S.C. 154(b) by 0 days.

(21) Appl. No.: 14/075,994

(22) Filed: Nov. 8, 2013

(65) Prior Publication Data

US 2014/0179617 A1    Jun. 26, 2014

Related U.S. Application Data

(63) Continuation of application No. 11/509,682, filed on Aug. 25, 2006, now abandoned, which is a continuation of application No. 10/720,603, filed on Nov. 24, 2003, now Pat. No. 7,491,394, which is a continuation-in-part of application No. 10/047,710, filed on Jan. 15, 2002, now Pat. No. 7,084,105.

(60) Provisional application No. 60/414,550, filed on Aug. 15, 2003, provisional application No. 60/269,133, filed on Feb. 15, 2001.

(51) Int. Cl.
| | | |
|---|---|---|
| *A61K 39/00* | (2006.01) | |
| *C07K 14/80* | (2006.01) | |
| *A61K 38/16* | (2006.01) | |
| *C07K 14/195* | (2006.01) | |
| *A61K 38/41* | (2006.01) | |

(52) U.S. Cl.
CPC ............ *C07K 14/80* (2013.01); *A61K 38/164* (2013.01); *A61K 38/168* (2013.01); *A61K 38/415* (2013.01); *C07K 14/195* (2013.01)

(58) Field of Classification Search
None
See application file for complete search history.

(56) References Cited

U.S. PATENT DOCUMENTS

| | | | |
|---|---|---|---|
| 5,681,810 A | 10/1997 | Villemez et al. | |
| 5,789,389 A | 8/1998 | Tarasewicz | |
| 5,972,899 A | 10/1999 | Zychlinsky et al. | |
| 6,551,795 B1 * | 4/2003 | Rubenfield et al. | 435/69.1 |

FOREIGN PATENT DOCUMENTS

EP   163990 B1   6/2010

OTHER PUBLICATIONS

Hantgan et al, JBC, 252:1367-74, 1977.*
Matsuura et al, J Mole Bo 156:389-409, 1982, abstract only.*
Goto et al Mol Micribiology 47:549-559, Jan. 2003.*
Ambler et al, Biochem J. 131:485-498, 1973 (Year: 1973).*
Zaborina et al, Microbiology 146:2521-2530, 2000 (Year: 2000).*
Translated Mexico Office Action dated Jan. 9, 2013, MX/a/2009/008297 pp. 1-2 (2013).
Canters et al, FEBS, 212:168-172, 1987.
Yamada et al PNAS, vol. 99, p. 14098-14103, 2002.
Hiraoka et al PNAS, vol. 101, p. 6427-6432, 2004.
Ambler et al, Biochem J. vol. 131, p. 485-498, 1973.
Arai et al FEBS vol. 261, p. 196-198, 1990.
Zaborina et al Microbiology 146:2521-2530, 2000.
Sequence search results (Rubenfield) 2009.
Ambler et al, Biochem. J. vol. 89: 349-378, 1963.
Sequence search result—1.
Sequence search result—2.
Sequence search result—3.
Sequence search result—ODP.
Christopher D. Buckley; Letter of Nature; 1999; vol. 397; pp. 534-539.
Gough Julian et al.; "The Linked Conservation of Structure and Function in a Family of High Diversity: The Monomeric Cupredoxins"; Structure (Cambridge); vol. 12; No. 6, Jun. 2004; pp. 917-925; XP002486972.
PCT International Application No. PCT/US02/01408—International Search Report.
Anomymous: Database EMBL Online!, Nov. 1, 1997, XP002306632 abstract.
Anomymous: Database EMBL Online!, Mar. 1, 1992, XP002306633 abstract.
Anomymous: Database EMBL Online!, Feb. 1, 1991, XP002306634 abstract.
Alexandroff, Anton B. et al., The Lancet, vol. 353, 1689-1694 (May 15, 1999).
Confer, A.W. and Durham, Janet A., Am. J. Res., vol. 53, No. 5. pp. 646-652 (1992).
Cutruzzola, F. et al., J. Inorganic Chemistry, 88, pp. 353-361 (2002).
Dang, L.H. et al., Proc. Nat. Acad. Sci. USA, 98, 15155-15160 (2001).
Goto, M. et al., Mol. Bio., 47(2), pp. 549-559 (2003).
Hunter, Christopher A. et al., The Journal of Immunology, 166: 5878-5881 (2001).
Jain, R.K., et al., Proc. Natl. Acad. Sci. USA 98, 14748-14750 (2001).
Kim, David H. et al., The Journal of Clinical Investigation, vol. 105, No. 7, 837-839 (2000).
Kukimoto et al., FEBS Letters, 394, pp. 87-90 (1996).
Melnikov, A. et al., Mol. Microbiol. 36: 1481-1493 (2000).
Murphy, L.M. et al., J. Mol. Biol., 315, pp. 859-871 (2002).

(Continued)

*Primary Examiner* — Lei Yao
(74) *Attorney, Agent, or Firm* — Benesch, Friedlander, Coplan & Aronoff LLP

(57) ABSTRACT

Cytotoxic factors having use in modulating cell death, and their use in methods of treating necrosis or apoptosis-related conditions are disclosed. The invention also relates to methods for identifying active agents useful in treating conditions related to cell death or uncontrolled growth. The present inventors have found that different microorganisms produce different cytotoxic factor(s) having anticancer activity. The substantially pure cytotoxic factors can be used in a method of treating an infectious disease or a cancer.

5 Claims, 16 Drawing Sheets

Specification includes a Sequence Listing.

(56) References Cited

OTHER PUBLICATIONS

O'Donnell, Michael A., Tibtech, vol. 15, 512-517 (Dec. 1997).
Paglia, Paola et al., The Journal of Immunology, 166: 5878-5881 (2001).
Pawelek, John H. et al., Cancer Research, vol. 57, 4537-4544 (1997).
Potera, Carol, ASM News, vol. 66, No. 6 (2000).
Punj, V. et al., Infect. Immun. 68: 4930-4937 (2000).
Punj, V. & Chakrabarty, A.M., Cellular Microbiology, 5(4), pp. 225-231 (2003).
Punj, V. et al., Biochemical and Biophysical Research Communications, vol. 312, pp. 109-114 (2003).
Punj, Vasu et al., Oncogene 2003—Proof copy.
Punj, Vasu et al., Oncogene (2004) 23, 2367-78.
Sznol, Mario et al., The Journal of Clinical Investigation, vol. 105, No. 8, 1027-1030 (2000).
Wu, T. et al., Antimicrobial Agents and Chemotherapy, vol. 44, No. 5, pp. 1200-1208 (May 2000).
Yamada, T. et al., Infection & Immunity, vol. 70. No. 12, pp. 7054-7062 (2002).
Zaborina, O. et al., Infect. Immun. 67: 5231-5242 (1999).
Zaborina et al., Molecular Microbiology (1999) 31 (5), 1333-1343.

\* cited by examiner

CYTOTOXIC FACTORS FOR MODULATING CELL DEATH

RELATED APPLICATIONS

This application is a Continuation of U.S. patent application Ser. No. 11/509,682, filed Aug. 25, 2006, now abandoned, which is a continuation of U.S. patent application Ser. No. 10/720,603, filed Nov. 24, 2003, issued on Feb. 17, 2009 as U.S. Pat. No. 7,491,394, which claims priority to U.S. Provisional Patent Application No. 60/414,550, filed Aug. 15, 2003, and is a continuation-in-part of U.S. patent application Ser. No. 10/047,710, filed Jan. 15, 2002, issued on Aug. 1, 2006 as U.S. Pat. No. 7,084,105, which claims priority to U.S. Provisional Patent Application Ser. No. 60/269,133, filed Feb. 15, 2001. The entire content of these prior applications is fully incorporated herein by this reference.

STATEMENT OF GOVERNMENTAL INTEREST

The subject matter of this application has been supported by research grants from the National Institutes of Health (NIH), Bethesda, Md., U.S.A., (Grant Numbers AI 16790-21, ES 04050-16, AI 45541, CA09432 and N01-CM97567). The government may have certain rights in this invention.

FIELD OF THE INVENTION

The present invention relates to cytotoxic factors secreted by microorganisms and inhibitors of cytotoxic factors and their use in causing cellular growth arrest and in modulating cell death by necrosis and apoptosis. The present invention also relates to methods of producing, isolating and identifying such cytotoxic factors and to compositions incorporating substantially pure cytotoxic factors useful in modulating cell death and causing cellular growth arrest. The invention also relates to methods of treating apoptosis-related conditions. More particularly, the invention relates to the use of a substantially pure cytotoxic factor in a method of inducing apoptosis or cellular growth arrest in a cancer cell and to the use of inhibitors of the cytotoxic factors for treating an infection or other pathogen-induced condition.

BACKGROUND

Infectious diseases can be a product of a number of environmental factors. Underlying any infectious disease is a causative infectious agent. The infectious agent typically is a pathogenic microorganism, for example, a pathogenic bacterium. The degree or ability of a pathogenic microorganism to overcome defense mechanisms and cause a disease is related to its virulence. Both pathogenic and non-pathogenic microorganisms are known to express cytotoxic factors, which allow the microorganism to defend itself from the host immune system and prevent phagocytes (e.g., macrophages and mast cells) from eliminating the microorganism from the body. When the pathogenic microorganisms survive, the microorganisms can invade the host tissues and proliferate, causing severe disease symptoms. Pathogenic bacteria have been identified as a root cause of a variety of debilitating or fatal diseases including, for example, tuberculosis, cholera, whooping cough, plague, and the like. To treat such severe infections, drugs, for example, antibiotics, are administered that either kill the infectious agent or disarm the cytotoxic factors so that the infectious agent is no longer able to defend itself against the host immune system. However, pathogenic bacteria commonly develop resistance to antibiotics and improved agents are needed to prevent the spread of infections due to such microorganisms.

A cancer is a malignant tumor of potentially unlimited growth. It is primarily the pathogenic replication (a loss of normal regulatory control) of various types of cells found in the human body. Initial treatment of the disease is often surgery, radiation treatment or the combination of these treatments, but locally recurrent and metastatic disease is frequent. Chemotherapeutic treatments for some cancers are available but these seldom induce long term regression. Hence, they are often not curative. Commonly, tumors and their metastases become refractory to chemotherapy, in an event known as the development of multidrug resistance. In many cases, tumors are inherently resistant to some classes of chemotherapeutic agents. In addition, such treatments threaten noncancerous cells, are stressful to the human body, and produce many side effects. Improved agents are therefore needed to prevent the spread of cancer cells.

Many cancers are known to regress when patients are infected with pathogenic bacteria. However, very little is known about how bacterial infections cause regression of human cancers.

SUMMARY

The present invention relates to cytotoxic factors that stimulate cell death by necrosis or apoptosis or that cause cellular growth arrest. In one aspect, substantially pure cytotoxic factors have been characterized and isolated. Substantially pure cytotoxic factors are obtained by column chromatographic fractionation of a growth medium which has been exposed to a pathogenic microorganism. Preferably, the production and secretion of such cytotoxic factors are stimulated during growth of pathogenic organisms in the presence of mammalian proteins.

In another aspect of the present invention, the identification of receptors for mammalian proteins as a means of delineating virulent and avirulent microorganisms can lead to improved specificity for disease treatment.

Yet another aspect of the present invention relates to a method of treating a condition related to cell death resistance or susceptibility comprising the step of administering a cytotoxic factor, an inhibitor of a cytotoxic factor, or a variant or derivative thereof, optionally incorporated in a pharmaceutical carrier.

The cytotoxic factor, or a variant or derivative thereof, can be incorporated into a pharmaceutical composition for use in the prevention and treatment of conditions related to abnormal cell proliferation. For example, a cytotoxic factor can be used to treat a cancer.

An inhibitor of a cytotoxic factor, or a variant or derivative thereof, can be used to treat a bacterial infection by preventing phagocytic cell death and hence allowing the host immune system to combat an invading pathogen.

In another embodiment of the present invention, cytotoxic factors, as well as components of their secretion machinery, can be used as candidates for vaccines against infectious agents.

The present invention also relates to a method of modulating cell death comprising the step of controlling secretion of cytotoxic factors. In one embodiment, the cytotoxic factors can be used as anti-cancer agents against a host of human cancer cells. Cytotoxic factors can also be used as targets for drug development through screening or rational design of inhibitors.

The present invention also relates to a method of modulating cell death comprising utilizing a cytotoxic factor such as an azurin, a plastocyanin, a rusticyanin, a pseudoazurin, or a cytochrome c551, or a mutant of such a cytotoxic factor.

These and other aspects, advantages, and features of the invention will become apparent from the following figures and detailed description of the preferred embodiments.

BRIEF DESCRIPTION OF THE FIGURES

FIGS. 11(a) and (b). FIG. 11(a) is a table showing the alignment of the amino acid sequence of *P. aeruginosa* azurin with other bacterial azurins. Amino acid sequences are aligned by Genetyx software. FIG. 11(b) is a table showing wild type azurin (wt azurin) and chimeric mutant azurins.

FIG. 12(a) is a graph showing the cytotoxicity of wild type and redox mutant azurins towards macrophage cells. Wild type azurin (●), apo-azurin (○), M44KM64E (▲), C112D (△).

FIG. 12(b) is a graph showing the cytotoxity of wild type and chimeric mutant azurins towards macrophage cells. Wild type azurin (●), S1(○), S2(▲), 53(■), S4 (A), S6(□), wtS5(▼), wtS5S4S6 (◆), 5355(▽). FIG. 12(b) also shows the relative electron transfer efficiency of the mutants expressed as a percentage of that of wild type azurin. To calculate percentage cytotoxicity, the number of nontreated viable cells was taken as 100% and the number of viable cells in the azurin-treated samples determined.

DETAILED DESCRIPTION OF THE EMBODIMENTS

Definitions

Figure 1:
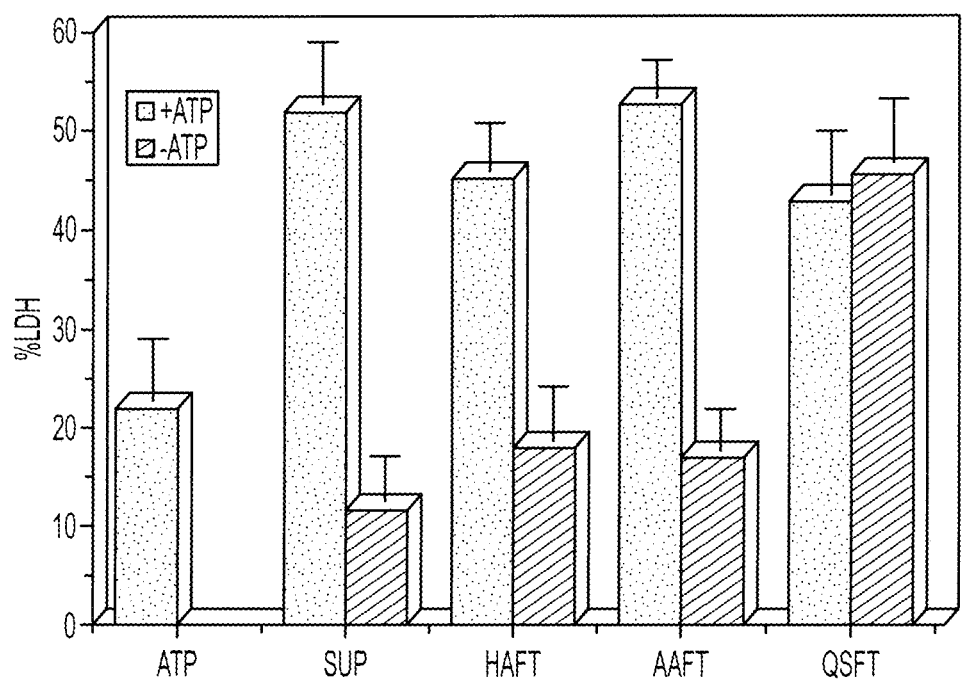
FIG. 1. Chart showing the effect of 1.0 mM ATP on macrophage killing in absence or in presence of the filtered growth medium supernatant (SUP) or the hydroxyapatite flow through (HAFT), ATP-agarose flow through (AAFT) and Q-sepharose flow through (QSFT) column chromatographic fractions derived from *B. cepacia* growth medium. The extent of macrophage cell death is measured by release of the intracellular enzyme lactate dehydrogenase (LDH). 2 μg of protein from each fraction was used in the assay. All assays were carried out in triplicate and error bars are indicated.
Figure 2:
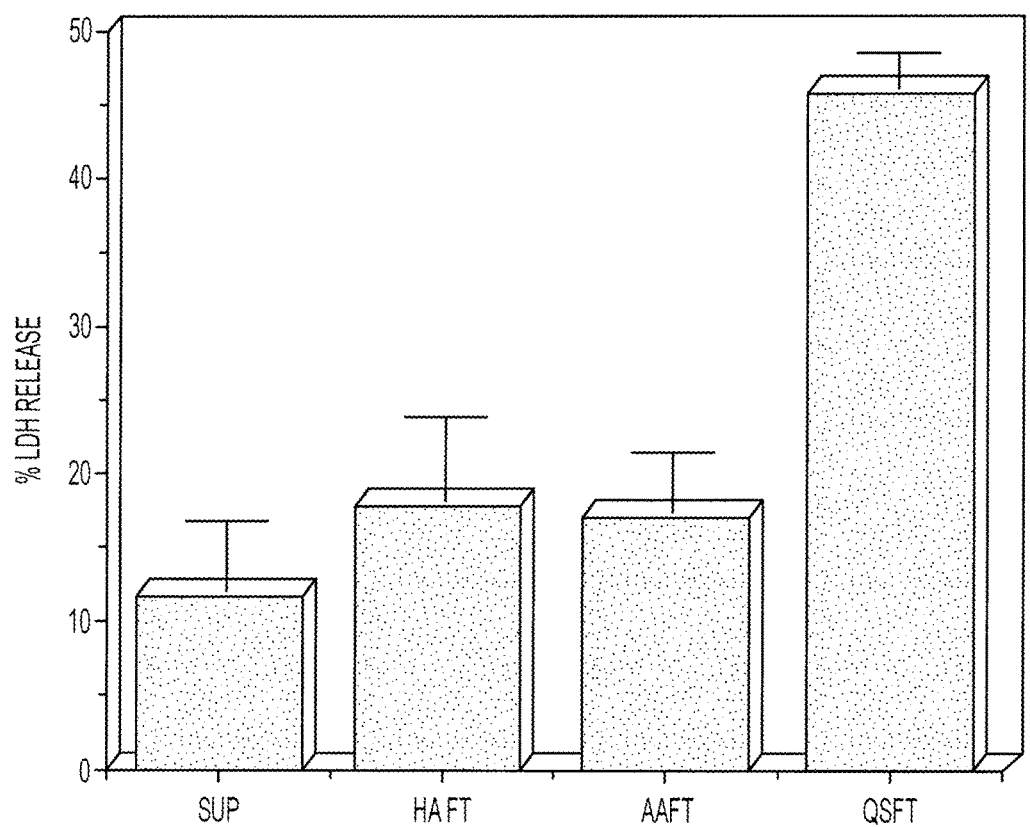
FIG. 2. Chart showing the effect of filtered growth medium supernatant (SUP) and column chromatographic fractions (HAFT, AAFT and QSFT) of *B. cepacia* on macrophage cell death in the absence of ATP. The extent of macrophage cell death is measured by the release of the intracellular enzyme lactate dehydrogenase (LDH). All assays were carried out in triplicate and error bars are indicated.

For the purposes of the description herein, the term "cytotoxic factor" refers to a factor secreted by a pathogenic or nonpathogenic microorganism and that stimulates cell death by necrosis or apoptosis or that causes cellular growth arrest. Examples of cytotoxic factors include an azurin, a plastocyanin, a rusticyanin, a pseudoazurin, or a cytochrome c551. The term "ATP-dependent", when used to modify the term "cytotoxic factor" refers to a cytotoxic factor which acts to cause cell death or cellular growth arrest in the presence of adenosine 5'-triphosphate (ATP). The term "ATP-independent", when used to modify the term "cytotoxic factor" refers to a cytotoxic factor which acts to cause cell death or cellular growth arrest in the absence of ATP.

For the purposes of the description herein, the term "treatment" includes preventing, lowering, stopping, or reversing the progression or severity of the condition or symptoms being treated. As such, the term "treatment" includes medical, therapeutic, and/or prophylactic administration, as appropriate.

As used herein, the term "a condition related to resistance to cell death" refers to a disease, state, or ailment characterized by at least a tendency for prolonged cell life when compared with a healthy cell of like kind as determined by a reasonable, skilled physician or clinician. The term "a condition related to cell death susceptibility", as used herein, refers to a disease, state, or ailment characterized by at least a tendency for premature cell death when compared with a healthy cell of like kind as determined by a reasonable, skilled physician or clinician.

As used herein, the term "having a functional p53 tumor suppressor gene" refers to a cell having a p53 tumor suppressor gene that is not inactivated, mutated, lost or under produced.

As used herein, the term "deficient in p53 tumor suppressor gene" refers to a cell having a p53 tumor suppressor gene that is inactivated, mutated, lost or under produced. For example, such a deficiency may occur as a result of genetic aberrations within the p53 gene or interaction with viral and cellular oncogenes.

The term "substantially pure", when used to modify the term "cytotoxic factor", as used herein, refers to a cytotoxic factor, for example, a cytotoxic factor isolated from the secreted growth medium, in a form substantially free of, or unadulterated by, active inhibitory compounds. The term "substantially pure" refers to a factor in an amount of at least about 75%, by weight, of isolated fraction, or at least "75% substantially pure". More preferably, the term "substantially pure" refers to a compound of at least about 85%, by weight, active compound, or at least "85% substantially pure". The substantially pure cytotoxic factor can be used in combination with one or more other substantially pure compounds or isolated cytotoxic factors.

As used herein, the term "a variant or derivative" of a cytotoxic factor refers to a compound or substance obtained by chemical modification or manipulation of the cytotoxic factor or the gene encoding the cytotoxic factor. The variant or derivative of a cytotoxic factor can be obtained by chemical modification of the cytotoxic factor, or by manipulation of genes encoding the cytotoxic factor, for example by altering the basic composition or characteristics of the cytotoxic factor, but not its toxicity. Similarly, "a variant or derivative" of an inhibitor of a cytotoxic factor can include chemical modifications to the chemical structure of the inhibitor or manipulation of genes encoding the inhibitor.

The term "percent (%) amino acid sequence identity" is defined as the percentage of amino acid residues in a cytotoxic factor that are identical with amino acid residues in a candidate sequence when the two sequences are aligned. To determine % amino acid identity, sequences are aligned and if necessary, gaps are introduced to achieve the maximum % sequence identity; conservative substitutions are not considered as part of the sequence identity Amino acid sequence alignment procedures to determine percent identity are well known to those of skill in the art. Often publicly available computer software such as BLAST, BLAST2, ALIGN2 or Megalign (DNASTAR) software is used to align peptide sequences.

When amino acid sequences are aligned, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as:

$$\% \text{ amino acid sequence identity} = X/Y \cdot 100$$

where

X is the number of amino acid residues scored as identical matches by the sequence alignment program's or algorithm's alignment of A and B and Y is the total number of amino acid residues in B.

If the length of amino acid sequence A is not equal to the length of amino acid sequence B, the % amino acid sequence identity of A to B will not equal the % amino acid sequence identity of B to A.

A "therapeutically effective amount" is an amount effective to prevent development of, or to alleviate the existing symptoms of, the subject being treated. Determination of a therapeutically effective amount is well within the capability of those skilled in the art.

General

The present invention provides cytotoxic factors that are secreted by pathogenic or nonpathogenic microorganisms and that stimulate cell death by necrosis or apoptosis or that cause cellular growth arrest. When pathogenic microorganisms invade human or animal tissues, phagocytic cells are a first line of defense in the host immune system. Typically, phagocytes seek out and destroy foreign pathogens invading the body. However, cytotoxic factors secreted by microbial pathogens can stimulate cell death in the phagocytic cells. Thus, the phagocytes are prevented from performing their protective immune function.

The inventors have previously reported that many pathogenic bacteria secrete ATP-dependent cytotoxic factors, for example ATP-utilizing enzymes, that cause phagocytic cell death by necrosis. [Zaborina O. et al., Infect. Immun. 67: 5231-5242 (1999); Melnikov A. et al., Mol. Microbiol. 36: 1481-1493 (2000); and Punj V. et al., *Infect. Immun.* 68: 4930-4937 (2000), the contents of which are incorporated for all purposes by the reference.] ATP-utilizing enzymes act on various energy-related nucleotide derivatives such as ATP, adenosine 5'-diphosphate (ADP), adenosine 5'-monophosphate (AMP), or adenosine, converting them to various products that in turn can modulate the death of phagocytic cells such as macrophages and mast cells through activation of purinergic receptors.

One aspect of the present invention relates to the discovery that ATP-independent cytotoxic factors, for example redox proteins, are also secreted by some species of pathogenic microorganisms, and that such factors cause phagocytic cell death by apoptosis. [Zaborina O. et al., *Microbiology* 146: 2521-2530 (2000), the contents of which are incorporated for all purposes by the reference.]

Another aspect of the present invention relates to the surprising discovery that ATP-independent cytotoxic factors induce apoptosis or cellular growth arrest in cancer cells. Such cytotoxic factors may be used to treat a condition related to resistance to cell death. Such conditions may include, for example, human melanoma, leukemia, breast cancer, ovarian cancer, lung cancer, mesenchymal cancer, colon cancer and aerodigestive tract cancers (e.g. stomach, esophagus, larynx and oral cancers).

Normally cancer cells are not susceptible to apoptotic death. Such resistance to cell apoptotic cell death can be caused by inactivating mutations in the gene encoding the p53 tumor suppressor protein. It is known that mammalian cell apoptosis requires the presence of p53 protein. However, in 50% of human cancers, inactivating mutations in the gene encoding the p53 tumor suppressor protein are present.

Although it is also known that p53 regulates the expression of redox proteins in mammalian cells, mammalian redox proteins have not been directly implicated in cancer cell apoptosis or growth arrest. Neither has the role of microbial ATP-independent cytotoxic factors in inducing apoptosis in cancer cells or in reducing tumor size been shown.

Another aspect of the present invention relates to methods of identification and characterization of cytotoxic factors secreted by microorganisms. Such methods can provide a means for discovering appropriate inhibitors or stimulators of cell death. Inhibitors and stimulators can be developed as pharmaceutical drugs and used to treat conditions characterized by resistance or susceptibility to cell death.

Another aspect of the invention relates to cytotoxic factors that have been characterized and isolated and to inhibitors of such cytotoxic factors. The cytotoxic factors can be activated or inactivated in accordance with a method of the invention to prevent or treat a condition related to cell death. An inhibitor of a cytotoxic factor can be used to treat a condition related to cell death susceptibility.

Secretion of Cytotoxic Factors

In one aspect of the present invention, cytotoxic factors of the present invention are secreted by a number of different pathogenic microorganisms, including bacteria and protozoa. Examples of pathogenic bacteria suitable for providing the cytotoxic factors include, but are not limited to, Pseudomonas aeruginosam (P. aeruginosa), Burkholderia cepacia (B. cepacia), Vibrio cholerae (V. cholerae), and Mycobacterium bovis (M. bovis). In addition, cytotoxic factors are secreted by pathogens, such as Leishmania amazonensis and Brugia malayi.

P. aeruginosa, an opportunistic pathogen, B. cepacia, which causes fatal infections in patients suffering from cystic fibrosis and chronic granulomatous disease, V. cholerae, the intestinal pathogen that causes cholera and the slow-growing virulent group of mycobacteria, such as M. tuberculosis or M. bovis, that cause tuberculosis have been found to secrete ATP-utilizing enzymes.

In addition to secreting ATP-utilizing enzymes, the inventors have found that P. aeruginosa secretes ATP-independent cytotoxic factors. These have been identified as two redox proteins, azurin and cytochrome $c_{551}$. B. cepacia has also been shown to secrete the redox proteins. M. bovis has been shown to also secrete cytotoxic factors having high ATP-independent cytotoxicity towards phagocytic cells.

Stimulation of the Secretion of Cytotoxic Factors in the Presence of Mammalian Proteins In another aspect of the present invention, production and secretion of cytotoxic factors are stimulated during growth of pathogenic organisms in the presence of mammalian proteins. For example, the secretion of cytotoxic factors by pathogenic microorganisms such as P. aeruginosa, M. bovis and B. cepacia is stimulated by the presence of mammalian proteins such as kappa-casein, bovine serum albumin, ovalbumin or α2-macroglobulin. It is suggested, but not relied upon herein, that the pathogenic microorganisms sense the presence of certain mammalian proteins as indicative of the mammalian host environment, thereby opening up the secretion machinery for the cytotoxic agents to counter and subvert host defense.

The inventors have determined that several clinical (virulent) isolates of B. cepacia secrete large amounts of ATP-utilizing enzymes such as adenylate kinase or 5'-nucleotidase, while several environmental (avirulent) isolates secreted only reduced amounts of these enzymes. In clinical isolates, such as B. cepacia strain 38, the level of secretion of cytotoxic factor is greatly enhanced in the presence of α2-macroglobulin in the growth medium. The secreted products from clinical isolates have a higher level of cytotoxicity towards macrophages and mast cells than that from environmental isolates. The clinical isolates that demonstrate enhanced secretion of cytotoxic factors in the presence of α2-macroglobulin also demonstrate the presence of the receptors for α2-macroglobulin on their surface.

In one embodiment of the present invention, the production and secretion of ATP-independent cytotoxic factors are stimulated during growth of microorganisms in the presence of mammalian proteins. Increased secretion of cytotoxic factors can be obtained by growing microorganisms organisms in growth media containing mammalian proteins. Suitable growth media are, for example, L broth, nutrient broth, Trypticase soy broth and tryptone-yeast extract broth (Difco Laboratories, Maryland, U.S.A.). Typically, approximately 500 ml to 1,000 ml of sterile autoclaved growth medium are inoculated with between about $10^4$ to $10^6$ cells/ml. The inoculated medium is then incubated under conditions suitable to allow growth of the microorganism, usually on a rotary shaker at 30° C. to 37° C. Selection of growth media, incubation conditions, and other factors allowing successful culture of bacteria and other microorganisms will be clearly apparent to one skilled in the art. The inventors have observed that maximum concentrations of cytotoxic factors in the growth medium occur late in the exponential growth phase and early in the stationary growth phase.

In another embodiment of the present invention, the identification of receptors for mammalian proteins provides a means of delineating virulent and avirulent strains of microorganisms. For example, the presence of the receptors for α2-macroglobulin primarily in clinical isolates, but not in environmental isolates, not only correlates with the ability of the former to secrete cytotoxic agents as weapons against the host defense, but also allows delineation between the clinical, virulent strains with the environmental, avirulent strains. Hence, virulent strains of organisms can be identified and then tested for their antibiotic sensitivity or for other clinical purposes.

Purification of ATP-Independent Cytotoxic Factors

In another aspect of the present invention, substantially pure ATP-independent cytotoxic factors are obtained by column chromatographic fractionation of the growth medium of the secreting microorganism. Preferably, the bacterial cells are removed from the growth medium prior to fractionation. This may be achieved by initial centrifugation and subsequent filtering the growth medium. Suitable filters are typically less than or equal to about 0.5 µm pore size and preferably about 0.2 µm. However, other methods of pathogen removal will be known to those skilled in the art.

Unfractionated growth media do not have high ATP-independent cytotoxic activity and hence column chromatographic fractionation is necessary to enhance apoptosis-inducing or cellular growth arresting activity. Fractionation removes ATP-dependent cytotoxic factors. It is also suggested, but not relied upon herein, that fractionation also removes inhibitors of ATP-independent cytotoxic factors that may be present in the unfractionated growth medium.

Chromatographic techniques useful in purifying cytotoxic factors will be known to those skilled in the art. These include, for example, ion-exchange chromatography, hydroxyapatite chromatography, affinity chromatography, and gel-filtration chromatography. Chromatographic columns useful in the fractionation of bacterial growth media include, for example: Hydroxyapatite; Superdex 75 or 200; Superose 6 or 12; Sephacryl S; Sephadex G or Sephadex LH; Mono Q or Mono S; Q-Sepharose; DEAE Sepharose or CM Sepharose; Sepharose XL; ATP-Sepharose; Hi Trap Blue; Blue Sepharose; DNA Cellulose or Sepharose 2B, 4B or 6B, available from Amersham Pharmacia Biotech AB, Uppsala, Sweden or Bio-Rad Laboratories, Hercules, Calif., U.S.A.

ATP-utilizing enzymes may be isolated by column chromatographic fractionation as flow-through or eluted fractions of hydroxyapatite and ATP-agarose columns. During such fractionation, the ATP-utilizing enzymes, such as ATPase or adenylate kinase are adsorbed on the column and can be removed or purified further. (See, for example, Markaryan et al., J. Bacteriol., 183, pp 3345-3352, 2001.)

In one embodiment of the present invention, ATP-independent cytotoxic factors are isolated as flow-through fractions of Q-sepharose columns (QSFT). Q-sepharose is a quaternary ammonium strong anion exchanger. Such columns can be obtained from Amersham Pharmacia Biotech AB, Uppsala, Sweden. The supernatant (SUP) or other column fractions such as hydroxyapatite column flow through fraction (HAFT) or ATP-agarose column flow through fraction (AAFT) do not normally show high ATP-independent cytotoxicity.

Characterization of ATP-Independent Cytotoxic Factors

In a further aspect of the present invention, fractionated growth media are tested to determine the presence of ATP-independent cytotoxic factors. The extent of cell death may be measured by the release of the intracellular enzyme lactate dehydrogenase (LDH) as described in Zaborina et al., Infection and Immunity, 67, 5231-5242 (1999) and Zaborina et al., Microbiology, 146, 2521-2530 (2000), the contents of which are incorporated for all purposes by this reference.

The ability of ATP-independent cytotoxic factors to induce apoptosis may be observed by mitosensor ApoAlert confocal microscopy using a MITOSENSOR™ APOLERT™ Mitochondrial Membrane Sensor kit (Clontech Laboratories, Inc., Palo Alto, Calif., U.S.A.). In the assay, healthy, non-apoptotic cells fluoresce red while apoptotically dead cells fluoresce green. A combination of red and green produces yellow fluorescing cells that represent apoptotically dying cells. See Zaborina et al., Microbiology, 146, 2521-2530 (2000), the contents of which are incorporated for all purposes by this reference.

Apoptosis is mediated via activation of a cascade of enzymes known as caspases, which are cysteine proteases cleaving at aspartic residues. Hence, apoptosis may also be detected by measuring two important caspase activities, namely that of caspase 9 and caspase-3, which are known to be activated during apoptosis by the oligomerization of the cytochrome c released from mitochondria with a cytosolic protein Apaf-1, using the method described in Zou et al., J. Biol. Chem., 274: 11549-11556 (1999), the contents of which are incorporated for all purposes by this reference.

Apoptosis may also be observed by detecting apoptosis-induced nuclear DNA fragmentation using, for example, the APOLERT DNA fragmentation kit (Clontech Laboratories, Inc., Palo Alto, Calif., U.S.A.). This assay is based on terminal deoxynuclotidyltransferase (Tdt)-mediated dUTP nick-end labeling (TUNEL), where Tdt catalyzes the incorporation of fluorescein-dUTP at the free 3'-hydroxyl ends of fragmented DNA in cells undergoing apoptosis. The incorporation of fluorescein-dUTP in the fragmented nuclear DNA generates green fluorescence which is detected by confocal microscopy.

In one embodiment of the present invention, fractionated growth media are tested to determine the ability of such fractions to induce apoptosis or cellular growth arrest. Such methods are useful in the identification and characterization of ATP-independent cytotoxic factors.

Identification of ATP-Independent Cytotoxic Factors

In another aspect, this invention provides characterized cytotoxic factors exhibiting ATP-independent apoptosis-triggering cytotoxicity or that cause cellular growth arrest. The inventors have found that the QSFT fraction of *P. aeruginosa* and *B. cepacia* is enriched with two proteins, azurin and cytochrome $c_{551}$. The identification of these two proteins is based on their separation on SDS-PAGE and identification of their N-terminal amino acid sequences. In contrast, SDS-PAGE analysis of the *M. bovis* QSFT fraction shows a thick 65 kDa band of bovine serum albumin (BSA), which is a constituent of the 7H9 medium used for growing *M. bovis*, as well as several bands of greater than 45 kDa molecular mass, but not the bands characteristic of cytochrome $c_{551}$ or azurin. (See Example 9.)

Azurin and/or cytochrome $c_{551}$ and the QSFT fractions exhibit apoptosis-triggering cytotoxicity towards phagocytic cells. In isolation, cytochrome $c_{551}$ causes cellular growth arrest. A purified azurin/cytochrome $c_{551}$ mixture, or the *B. cepacia* QSFT fraction, treated with a mixture of anti-azurin and anti-cytochrome $c_{551}$ antibodies, show greatly diminished macrophage cytotoxicity. In contrast, the *M. bovis* QSFT fraction, when pretreated with anti-azurin/anti-cytochrome $c_{551}$ antibodies, shows very little reduction in cytotoxicity, confirming that *M. bovis* QSFT fraction contains cytotoxic factors other than azurin or cytochrome $c_{551}$. Thus different pathogens secrete different apoptosis-inducing or cellular growth arresting cytotoxic factors, all of which would be excellent targets for drug development.

ATP-Independent Cytotoxic Factors

I. Cupredoxin Compounds

These small blue copper proteins (cupredoxins) are electron transfer proteins (10-20 kDa) that participate in bacterial redox chains, photosynthesis or are of unknown function. The copper ion is solely bound by the protein matrix. A special distorted trigonal planar arrangement to two histidine and one cysteinate ligands around the copper gives rise to very peculiar electronic properties of the metal site and an intense blue color. A number of cupredoxins have been crystallographically characterized at medium to high resolution.

Azurin

The azurins are copper containing proteins of 128 amino acid residues which belong to the family of cupredoxins involved in electron transfer in plants and certain bacteria. The azurins include those from *P. aeruginosa* (PA) (SEQ ID NO: 1), *A. xylosoxidans*, and *A. denitrificans*. Murphy, L. M. et al., J. Mol. Biol., vol. 315, pp 859-71 (2002), the contents of which are incorporated for all purposes by this reference. Although the sequence homology between the azurins varies between 60-90%, the structural homology between these molecules is high. All azurins have a characteristic β-sandwich with Greek key motif and the single copper atom is always placed at the same region of the protein. In addition, azurins possess an essentially neutral hydrophobic patch surrounding the copper site (Murphy et al.).

Plastocyanins

The plastocyanins are soluble proteins of eukaryotic plants that contain one molecule of copper per molecule and are blue in their oxidized form. They occur in the chloroplast, where they function as electron carriers. Since the determination of the structure of poplar plastocyanin in 1978, the structure of algal (*Scenedesmus, Enteromorpha, Chlamydomonas*) and plant (French bean) plastocyanins has been determined either by crystallographic or NMR methods, and the poplar structure has been refined to 1.33 Å resolution. SEQ ID NO: 2 shows the amino acid sequence of plastocyanin from *Phormidium laminosum*.

Despite the sequence divergence among plastocyanins of algae and vascular plants (e.g., 62% sequence identity between the *Chlamydomonas* and poplar proteins), the three-dimensional structures are conserved (e.g., 0.76 Årms deviation in the C alpha positions between the *Chlamydomonas* and Poplar proteins). Structural features include a distorted tetrahedral copper binding site at one end of an eight-stranded antiparallel beta-barrel, a pronounced negative patch, and a flat hydrophobic surface. The copper site is optimized for its electron transfer function, and the negative and hydrophobic patches are proposed to be involved in recognition of physiological reaction partners. Chemical modification, cross-linking, and site-directed mutagenesis experiments have confirmed the importance of the negative and hydrophobic patches in binding interactions with cytochrome f, and validated the model of two functionally significant electron transfer paths in plastocyanin. One putative electron transfer path is relatively short (approximately 4 Å) and involves the solvent-exposed copper ligand His-87 in the hydrophobic patch, while the other is more lengthy (approximately 12-15 Å) and involves the nearly conserved residue Tyr-83 in the negative patch, Redinbo et al., J. Bioenerg. Biomembr., vol. 26(1), pp 49-66 (1994) the contents of which are incorporated for all purposes by this reference.

Rusticyanins

Rusticyanins are blue-copper containing single-chain polypeptides obtained from a *Thiobacillus*. The X-ray crystal structure of the oxidized form of the extremely stable and highly oxidizing cupredoxin rusticyanin from *Thiobacillus ferrooxidans* (SEQ ID NO: 3) has been determined by multiwavelength anomalous diffraction and refined to 1.9 Å resolution. The rusticyanins are composed of a core beta-sandwich fold composed of a six- and a seven-stranded b-sheet. Like other cupredoxins, the copper ion is coordinated by a cluster of four conserved residues (His 85, Cys138, His143, Met148) arranged in a distorted tetrahedron. Walter, R. L. et al., J. Mol. Biol., vol. 263, pp-730-51 (1996) the contents of which are incorporated for all purposes by this reference.

Pseudoazurins

The pseudoazurins are a family of blue-copper containing single-chain polypeptide. The amino acid sequence of pseudoazurin obtained from *Achromobacter cycloclastes* is shown in SEQ ID NO: 4. The X-ray structure analysis of pseudoazurin shows that it has a similar structure to the azurins although there is low sequence homology between these proteins. Two main differences exist between the overall structure of the pseudoazurins and azurins. There is a carboxy terminus extension in the pseudoazurins, relative to the aruzins, consisting of two alpha-helices. In the midpeptide region azurins contain an extended loop, shortened in the pseudoazurins, which forms a flap containing a short α-helix. The only major differences at the copper atom site are the conformation of the MET side-chain and the Met-S copper bond length, which is significantly shorter in pseudoazurin than in azurin.

II Cytochrome $C_{551}$

Cytochrome $C_{551}$ from *P. aeruginosa* (Pa-$C_{551}$) is a monomeric redox protein of 82 amino-acid residues (SEQ ID NO: 5), involved in dissimilative denitrification as the physiological electron donor of nitrite reductase. The functional properties of Pa-$C_{551}$ have been extensively investigated. The reactions with non-physiological small inorganic redox reactants and with other macromolecules, like blue copper proteins, eukaryotic cytochrome c and the physiological partner nitrite reductase have provided a test for protein-protein electron transfer.

The three-dimensional structure of Pa-$C_{551}$, which is a member of bacterial class I cytochromes, shows a single low-spin heme with His-Met ligation and the typical polypeptide fold which however leaves the edges of pyrrole rings II and III of the heme exposed (Cutruzzola et al., J. Morgan. Chem., vol 88, pp 353-61 (2002) the contents of which are incorporated for all purposes by this reference). The lack of a 20-residue omega loop, present in the mammalian class I cytochromes, causes further exposure of the heme edge at the level of propionate 13. The distribution of charged residues on the surface of Pa-$C_{551}$ is very anisotropic: one side is richer in acidic residues whereas the other displays a ring of positive side chains, mainly lysines, located at the border of a hydrophobic patch which surrounds the heme crevice. This patch comprises residues Gly11, Val13, Ala14, Met22, Val23, Pro58, Ile59, Pro60, Pro62, Pro63 and Ala65. The anisotropic charge distribution leads to a large dipolar moment which is important for electron transfer complex formation.

The charge distribution described above for Pa-$C_{551}$ has been reported for other electron transfer proteins and their electron acceptors. Moreover, modification by site-directed mutagenesis of residues within the hydrophobic or charged patch has shown for different proteins the importance of surface complementarity for binding and electron transfer. As an example, evidence for the relevance of the hydrophobic patch for the electron transfer properties of azurin from *P. aeruginosa* came from the studies carried out on mutants of residues Met44 and Met64 changed to positively and negatively charged amino acids. (Cutruzzola et al.)

Induction of Apoptosis or Growth Arrest in Cancer Cells by ATP-Independent Cytotoxic Factors The present invention provides methods of using ATP-independent cytotoxic factors to induce apoptotic cell death or cellular growth arrest in cancer cells. ATP-independent cytotoxic factors, such as the cupredoxin compounds and cytochrome $C_{551}$, can be used to treat conditions related to an abnormal failure of cell death. It is well known that cancer cells are not prone to undergoing apoptosis. In accordance with one aspect of the present invention, administering a cytotoxic factor or active agent stimulating cytotoxic factor secretion in an amount sufficient to induce cancer cell apoptosis or cellular growth arrest would be beneficial in reducing tumor size in vivo and retarding the growth of tumors. For example, tests comparing azurin and cytochrome $C_{551}$ to a known anti-melanoma cancer drug [5-(3,3'-N,N'-dimethyl triazen-1-yl)-imidazole-4-carboxyamide] (DTIC) show that a mixture of azurin and cytochrome $C_{551}$ provides a potent, non-toxic composition that promotes tumor regression in vivo in nude mice.

In one embodiment of the invention, a method is provided wherein treatment with a cupredoxin compound, such as azurin, induces apoptotic cell death in cancer cells. While not wishing to be bound by theory, it is believed that the cytotoxic activity of the cupredoxin compound results from its ability to form a complex with, and stabilize, the tumor suppressor protein p53. p53 acts as a "tumor suppressor" gene and its under production or inactivation through mutation can lead to tumor development.

The half-life of p53 within a cell is normally only a few minutes. Stabilization of p53 allows the significant generation of reactive oxygen species (ROS) which is a potent inducer of apoptosis. Azurin forms a complex with p53, stabilizes it, and enhances its intracellular level, thereby inducing apoptosis via caspase-3 and capase-9-dependent mitrochondrial pathways Yamada, T. et al., Infec. Immun., vol. 70, pp 7054-62 (2002), the contents of which are incorporated for all purposes by this reference.

The redox activity of azurin is not critical for its cytotoxic activity. Instead, generation of reactive oxygen species during complex formation is the inducing factor for apoptosis. Goto, M. et al., Mol. Microbiol., 47, pp 549-59 (2003) the contents of which are incorporated for all purposes by this reference. For example, apo-azurin, which has an amino acid sequence SEQ ID NO: 1 but does not contain a copper atom, has a much lower redox activity compared to azurin but demonstrates significant cytotoxic activity.

The importance of complex formation with p53 is illustrated by differences in the cytotoxic activity of two mutant azurins, C112D (SEQ ID NO. 6) and the double mutant M44KM64E (SEQ ID NO. 7). The binding of copper to the Cys-112 residue is important for the redox activity. The C112D mutant, which is defective in co-ordinating with copper, has a redox activity of approximately 0.01% of azurin but shows significant cytotoxicity. In comparison, the M44KM64E mutant has a redox activity of approximately 2% of azurin but shows little cytotoxicity.

The azurin molecule contains a hydrophobic patch that is the interaction site of the physiological partners cytochrome $C_{551}$ and nitrite reductase. (Cutruzzola et al.) The C112D mutant, in with the hydrophobic patch is unchanged, is capable of forming complexes with p53 and raising its intracellular level. However, the M44KM64E double mutant, where an electric dipole is created in the hydrophobic patch, is not capable of forming such stable complexes. Thus, the interaction site with cytochrome $C_{551}$ and nitrite reductase is also important for complex formation with p53.

The glycerol gradient centrifugation and Glutathione S-transferase (GST) pull-down methods have been used to show the interaction of cupredoxin compounds with p53. Yamada et al. (2002), the contents of which are incorporated for all purposes by this reference. p53 is known to form oligomeric complexes and a GST-p53 fusion protein sediments at various glycerol fractions, such as 5, 10, 15, 20, or 25% glycerol, while azurin sediments at 5% glycerol. Prior incubation of azurin with the GST-p53 fusion protein followed by centrifugation in the glycerol gradient demonstrates the presence of azurin in all glycerol fractions, indicating its association with p53. The C112D mutant, but not the M44KM64E mutant, showed similar association. Yamada et al. (2002).

Preincubation of the GST-p53 fusion protein with the M44KM64E mutant azurin altered p53 oligomerization, resulting in most of the GST-p53 being found at 5 to 10% glycerol, where the mutant azurin protein was also found. This indicates that the hydrophobic patch of azurin is also involved in p53 interaction. A loss of azurin hydrophobicity not only results in a loss in cytotoxicity but also interferes with oligomerization. Although the M44KM64E mutant shows little induction of apoptosis, it does show significant inhibition of cell cycle progression. Thus, a change in the nature of the p53-cupredoxin complex can shift the specificity of p53 from apoptosis to cellular growth arrest.

The action of azurin is dependent upon the tumor cell having a functional p53 tumor suppressor gene. However, cytotoxic factors can also cause retardation in the growth of cells having a deficient p53 tumor suppressor gene. For example, cytochrome $C_{551}$ does not act on p53 but does significantly enhance the level of the tumor suppressor protein p16. $C_{551}$ inhibits cell cycle progression on macrophages and also enhances the effect of azurin. In addition, combinations of cytotoxic factors such as azurin and $C_{551}$ (or M44KM64E) can achieve more effective inhibition of tumor progression by inducing both apoptosis and growth arrest.

Because the mode of action of cytochrome $C_{551}$ is independent of the status of p53 in the cell, it provides for a method of cancer regression in the 50% of human cancers that have a deficient in p53 tumor suppressor gene. In addition to $C_{551}$, other cytochromes, for example, cytochrome f from cyanobacteria also demonstrate cytotoxicity.

Cytotoxic Factors in the Treatment of Infectious Disease

In another aspect of the present invention, characterization of cytotoxic factors can be useful for identifying new substances that inhibit cell death, for example, in an infectious disease. For example, inhibition of the secretion or activity of an ATP-utilizing cytotoxic factor, or the production of ATP, can reduce or eliminate cytotoxic activity by a disease-causing pathogen.

Accordingly, appropriately administering a compound that inhibits the secretion or activity of a cytotoxic factor provides a useful tool for anti-infective development. Examples of active agents useful for inhibiting activity of cell death inducing cytotoxic factor can include antibodies for cytotoxic factors, as well as analogues of ATP that prevent the activation of ATP-utilizing enzymes. Examples of cytotoxic factors and active agents for inhibiting or stimulating cytotoxic factor secretion or expression include, but are not limited to, ATP-utilizing enzymes, redox proteins, activators of ATP-production, inhibitors of ATP production, activators of redox proteins, and inhibitors of redox proteins.

Pharmaceutical Compositions Comprising Cytotoxic Factors

Pharmaceutical compositions comprising cytotoxic factors can be manufactured in any conventional manner, e.g. by conventional mixing, dissolving, granulating, dragee-making, emulsifying, encapsulating, entrapping, or lyophilizing processes. The substantially pure cytotoxic factor or other agent can be readily combined with a pharmaceutically acceptable carrier well-known in the art. Such carriers enable the preparation to be formulated as a tablet, pill, dragee, capsule, liquid, gel, syrup, slurry, suspension, and the like. Suitable excipients can also include, for example, fillers and cellulose preparations. Other excipients can include, for example, flavoring agents, coloring agents, detackifiers, thickeners, and other acceptable additives, adjuvants, or binders.

The compositions of the invention can be used in treatment of a condition related to cell death or in the prevention thereof. The substantially pure cytotoxic factor can be administered in an amount sufficient to prevent or treat a condition related to cell death. Typically, the host organism is a mammal, such as a human or animal.

Administration of Compositions Comprising Cytotoxic Factors

The compositions of the present invention can be administered by any suitable route, for example, by oral, buccal, inhalation, sublingual, rectal, vaginal, transurethral, nasal, topical, percutaneous, i.e., transdermal or parenteral (including intravenous, intramuscular, subcutaneous and intracoronary) administration. The compositions and pharmaceutical formulations thereof can be administered in any amount effective to achieve its intended purpose. More specifically, the composition is administered in a therapeutically effective amount.

In various embodiments, the cytotoxic factor composition includes carriers and excipients (including but not limited to buffers, carbohydrates, mannitol, proteins, polypeptides or amino acids such as glycine, antioxidants, bacteriostats, chelating agents, suspending agents, thickening agents and/or preservatives), water, oils, saline solutions, aqueous dextrose and glycerol solutions, other pharmaceutically acceptable auxiliary substances as required to approximate physiological conditions, such as buffering agents, tonicity adjusting agents, wetting agents and the like. It will be recognized that, while any suitable carrier known to those of ordinary skill in the art may be employed to administer the compositions of this invention, the type of carrier will vary depending on the mode of administration. Compounds may also be encapsulated within liposomes using well-known technology. Biodegradable microspheres may also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252.

The compositions of the invention may be sterilized by conventional, well-known sterilization techniques, or may be sterile filtered. The resulting aqueous solutions may be packaged for use as is, or lyophilized, the lyophilized preparation being combined with a sterile solution prior to administration.

The cytotoxic factor compositions of the invention may be administered in a variety of ways, including by injection (e.g., intradermal, subcutaneous, intramuscular, intraperitoneal and the like), by inhalation, by topical administration, by suppository, by using a transdermal patch or by mouth.

When administration is by injection, the cytotoxic factor may be formulated in aqueous solutions, preferably in physiologically compatible buffers such as Hanks solution, Ringer's solution, or physiological saline buffer. The solution may contain formulatory agents such as suspending, stabilizing and/or dispersing agents. Alternatively, the cytotoxic factor composition may be in powder form for constitution with a suitable vehicle, e.g., sterile pyrogen-free water, before use.

When administration is by inhalation, the cytotoxic factors may be delivered in the form of an aerosol spray from pressurized packs or a nebulizer with the use of a suitable propellant, e.g., dichlorodifluoromethane, trichlorofluoromethane, carbon dioxide or other suitable gas. In the case of a pressurized aerosol, the dosage unit may be determined by providing a valve to deliver a metered amount. Capsules and cartridges of, e.g., gelatin for use in an inhaler or insufflator may be formulated containing a powder mix of the proteins and a suitable powder base such as lactose or starch.

When administration is by topical administration, the cytotoxic factor composition may be formulated as solutions, gels, ointments, creams, suspensions, and the like, as are well known in the art. In some embodiments, administration is by means of a transdermal patch. When administration is by suppository (e.g., rectal or vaginal), cytotoxic factor compositions may also be formulated in compositions containing conventional suppository bases.

When administration is oral, a cytotoxic factor composition can be readily formulated by combining the cytotoxic factor with pharmaceutically acceptable carriers well known in the art. A solid carrier, such as mannitol, lactose, magnesium stearate, and the like may be employed; such carriers enable the chemotaxin to be formulated as tablets, pills, dragees, capsules, liquids, gels, syrups, slurries, suspensions and the like, for oral ingestion by a subject to be treated. For oral solid formulations such as, for example, powders, capsules and tablets, suitable excipients include fillers such as sugars, cellulose preparation, granulating agents, and binding agents.

Nucleic acid molecules encoding cytotoxic factors, can be inserted into vectors and used as gene therapy vectors. Gene therapy vectors can be delivered to a subject by, for example, intravenous injection, local administration (Nabel et al., U.S. Pat. No. 5,328,470 1994. USA), or by stereotactic injection (Chen et al., Proc Natl Acad Sci USA, vol. 91, pp 3054-7 (1994). The pharmaceutical preparation of a gene therapy vector can include an acceptable diluent or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

Other convenient carriers, as well-known in the art, also include multivalent carriers, such as bacterial capsular polysaccharide, a dextran or a genetically engineered vector. In addition, sustained-release formulations that include cytotoxic factor molecules allow for the release of cytotoxic factors over extended periods of time, such that without the sustained release formulation, the cytotoxic factor would be cleared from a subject's system, and/or degraded by, for example, proteases and simple hydrolysis before eliciting or enhancing an therapeutic effect.

The exact formulation, route of administration, and dosage is determined by the attending physician in view of the patient's condition. Dosage amount and interval can be adjusted individually to provide plasma levels of the active cytotoxic factor which are sufficient to maintain therapeutic effect. Generally, the desired cytotoxic factor is administered in an admixture with a pharmaceutical carrier selected with regard to the intended route of administration and standard pharmaceutical practice. Pharmaceutical compositions used in accordance with the present invention can be formulated in a conventional manner using one or more physiologically acceptable carriers comprising excipients and auxiliaries that facilitate processing of the cytotoxic factor, active agents, for inhibiting or stimulating the secretion of cytotoxic factors, or a mixture thereof into preparations which can be used therapeutically.

In one aspect, the cytotoxic factor is delivered as DNA such that the polypeptide is generated in situ. In one embodiment, the DNA is "naked," as described, for example, in Ulmer et al., Science, vol. 259, pp-1745-49 (1993) and reviewed by Cohen, Science, vol. 259, pp-1691-92 (1993). The uptake of naked DNA may be increased by coating the DNA onto a carrier, e.g. biodegradable beads, which is efficiently transported into the cells. In such methods, the DNA may be present within any of a variety of delivery systems known to those of ordinary skill in the art, including nucleic acid expression systems, bacterial and viral expression systems. Techniques for incorporating DNA into such expression systems are well known to those of ordinary skill in the art. See, e.g., WO90/11092, WO93/24640, WO 93/17706, and U.S. Pat. No. 5,736,524.

Vectors, used to shuttle genetic material from organism to organism, can be divided into two general classes: Cloning vectors are replicating plasmid or phage with regions that are non-essential for propagation in an appropriate host cell and into which foreign DNA can be inserted; the foreign DNA is replicated and propagated as if it were a component of the vector. An expression vector (such as a plasmid, yeast, or animal virus genome) is used to introduce foreign genetic material into a host cell or tissue in order to transcribe and translate the foreign DNA, such as the DNA of a cytotoxic factor. In expression vectors, the introduced DNA is operably-linked to elements such as promoters that signal to the host cell to transcribe the inserted DNA. Some promoters are exceptionally useful, such as inducible promoters that control gene transcription in response to specific factors. Operably-linking a cytotoxic factor polynucleotide to an inducible promoter can control the expression of the cytotoxic factor polypeptide or fragments. Examples of classic inducible promoters include those that are responsive to α-interferon, heat shock, heavy metal ions, and steroids such as glucocorticoids (Kaufman, Methods Enzymol., vol. 185, pp. 487-511 (1990)) and tetracycline. Other desirable inducible promoters include those that are not endogenous to the cells in which the construct is being introduced, but, however, are responsive in those cells when the induction agent is exogenously supplied. In general, useful expression vectors are often plasmids. However, other forms of expression vectors, such as viral vectors (e.g., replication defective retroviruses, adenoviruses and adeno-associated viruses) are contemplated.

Vector choice is dictated by the organism or cells being used and the desired fate of the vector. In general, vectors comprise signal sequences, origins of replication, marker genes, enhancer elements, promoters, and transcription termination sequences.

Kits Comprising Cytotoxic Factors

In one aspect, the invention provides kits containing one or more of the following in a package or container: (1) a biologically active composition comprising a cytotoxic factor; (2) a pharmaceutically acceptable adjuvant or excipient; (3) a vehicle for administration, such as a syringe; (4) instructions for administration. Embodiments in which two or more of components (1)-(4) are found in the same container are also contemplated.

When a kit is supplied, the different components of the composition may be packaged in separate containers and admixed immediately before use. Such packaging of the components separately may permit long-term storage without losing the active components' functions.

The reagents included in the kits can be supplied in containers of any sort such that the life of the different components are preserved and are not adsorbed or altered by the materials of the container. For example, sealed glass ampules may contain lyophilized cytotoxic polypeptide or polynucleotide, or buffers that have been packaged under a neutral, non-reacting gas, such as nitrogen. Ampules may consist of any suitable material, such as glass, organic polymers, such as polycarbonate, polystyrene, etc., ceramic, metal or any other material typically employed to hold similar reagents. Other examples of suitable containers include simple bottles that may be fabricated from similar substances as ampules, and envelopes, that may comprise foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to be mixed. Removable membranes may be glass, plastic, rubber, etc.

Kits may also be supplied with instructional materials. Instructions may be printed on paper or other substrate, and/or may be supplied as an electronic-readable medium, such as a floppy disc, CD-ROM, DVD-ROM, Zip disc, videotape, audiotape, etc. Detailed instructions may not be physically associated with the kit; instead, a user may be directed to an internet web site specified by the manufacturer or distributor of the kit, or supplied as electronic mail.

Stimulation and Inhibition of the Secretion of Cytotoxic Factors.

The identification and characterization of the cytotoxic factors also can lead to the development of methods of stimulating of cytotoxic factor secretion. Pathogenic organisms have been shown to secrete large amounts of cytotoxic factors in the presence of mammalian proteins. This principle can be modified in the human body to provide new methods of stimulating desired, or inhibiting undesired, cytotoxic factor production. Such methods are useful for inhibiting or stimulating cell apoptosis or causing cellular growth arrest. An understanding of cytotoxic factors, and the characterization and development thereof, also allows for drug development and screening of active agents or compounds suitable for modulating the cytotoxic factor activity or secretion. The understanding of the secretion machinery related to cytotoxic factor secretion in cells additionally provides new avenues of developing and identifying the design of useful inhibitors or stimulators of cytotoxic factors. The delineation and identification of the presence of receptors for mammalian proteins also can be used as a means to differentiate between the virulent and avirulent microorganisms, which can provide specificity in treating the disease.

Modification of Cytotoxic Factors.

Cytotoxic factors also can be chemically modified or genetically altered to produce variants that lack an ATP-utilizing enzyme or redox activity, but retain toxicity. Mutations and/or truncations of cytotoxic factors can produce cytotoxic agents of varying compositions also demonstrating functional activity. In particular, truncated derivatives with high efficacy and low antigenicity can be produced from the original cytotoxic factor. Such modified or altered cytotoxic factors also are included in the scope of the present invention.

Various derivatives of cytotoxic factors may be synthesized by standard techniques. Derivatives are amino acid sequences formed from native compounds either directly or by modification or partial substitution. Analogs are amino acid sequences that have a structure similar, but not identical, to the native compound but differ from it in respect to certain components or side chains. Analogs may be synthesized or from a different evolutionary origin.

Derivatives and analogs may be full length or other than full length, if the derivative or analog contains a modified amino acid. Derivatives or analogs of the cytotoxic factors include, but are not limited to, molecules comprising regions that are substantially homologous to the cytotoxic factors by at least about 65%, 70%, 75%, 85%, 90%, 95%, 98%, or 99% identity over an amino acid sequence of identical size or when compared to an aligned sequence in which the alignment is performed by a homology algorithm.

In addition to naturally-occurring allelic variants of cytotoxic factors, changes can be introduced by mutation into cytotoxic factors that incur alterations in the amino acid sequences of the encoded cytotoxic factors that do not significantly alter the cytotoxic activity. A "non-essential" amino acid residue is a residue that can be altered from the wild-type sequences of the cytotoxic factors without altering biological activity, whereas an "essential" amino acid residue is required for such biological activity. For example, amino acid residues that are conserved among the cytotoxic factors of the invention are predicted to be particularly non-amenable to alteration Amino acids for which conservative substitutions can be made are well known in the art.

Useful conservative substitutions are shown in Table 1, "Preferred substitutions." Conservative substitutions whereby an amino acid of one class is replaced with another amino acid of the same type fall within the scope of the invention so long as the substitution does not materially alter the biological activity of the compound.

TABLE 1

Preferred substitutions

| Original residue | Exemplary substitutions | Preferred substitutions |
| --- | --- | --- |
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

Non-conservative substitutions that affect (1) the structure of the polypeptide backbone, such as a β-sheet or α-helical conformation, (2) the charge, (3) hydrophobicity, or (4) the bulk of the side chain of the target site can modify the cytotoxic factor function. Residues are divided into groups based on common side-chain properties as denoted in Table 2. Non-conservative substitutions entail exchanging a member of one of these classes for another class. Substitutions may be introduced into conservative substitution sites or more preferably into non-conserved sites.

TABLE 2

Amino acid classes

| Class | Amino acids |
| --- | --- |
| hydrophobic | Norleucine, Met, Ala, Val, Leu, Ile |

TABLE 2-continued

Amino acid classes

| Class | Amino acids |
| --- | --- |
| neutral hydrophilic | Cys, Ser, Thr |
| acidic | Asp, Glu |
| basic | Asn, Gln, His, Lys, Arg |
| disrupt chain conformation | Gly, Pro |
| aromatic | Trp, Tyr, Phe |

The variant polypeptides can be made using methods known in the art such as oligonucleotide-mediated (site-directed) mutagenesis, alanine scanning, and PCR mutagenesis. Site-directed mutagenesis (Carter, Biochem J., vol. 237, pp 1-7 (1986); Zoller and Smith, Methods Enzymol., vol. 154, pp 329-50 (1987)), cassette mutagenesis, restriction selection mutagenesis (Wells et al., Gene, vol. 34, pp 315-23 (1985)) or other known techniques can be performed on the cloned DNA to produce the cytotoxic factor variant DNA.

The cytotoxic activity of the C112D and M44KM64E cytotoxic factor mutants is described above. In addition, Example 19 shows the cytotoxic activity of a number of chimeric azurin mutants prepared by site-directed mutagenesis as described in Example 18. The present invention can also utilize cytotoxic factors, such as apo-azurin, in which a copper atom is not present. Both apo-azurin and the C112D mutant show significant cytotoxic activity whereas the M44KM64E mutant does not. However, the M44KM64E mutant does cause significant inhibition of cell cycle progression.

One embodiment of the present invention utilizes mutated cytotoxic factors retaining the ability to form a complex with and stabilize p53 and hence induce apoptosis. In another embodiment, the present invention utilizes mutated cytotoxic factors, such as the M44KM64E mutant, having the ability to interact with p53 and cause cellular growth arrest.

A more complete understanding of the present invention can be obtained by reference to the following specific Examples. The Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations. Modifications and variations of the invention as hereinbefore set forth can be made without departing from the spirit and scope thereof, and, therefore, only such limitations should be imposed as are indicated by the appended claims.

EXAMPLES

Example 1. Stimulation of the Secretion of Cytotoxic Factors by Mammalian Proteins Clinical and environmental isolates (five of each) of *B. cepacia* were grown in proteose peptone-yeast extract (PPY) broth with and without added α2-macroglobulin (1 mg/ml). After growth for 10 hours at 34° C. on a shaker, a portion of the growth medium from each culture was centrifuged and the supernatant filtered through a 0.22 μm millipore filter to remove whole cells and debri. The filtered supernatant was then tested for adenylate kinase activity as described in Melnikov A. et al., Mol. Microbiol., 36: 1481-1493 (2000). Adenylate kinase transfers the terminal phosphate from

[γ-$^{32}$P]ATP to AMP giving rise to ADP. The products of this reaction were then detected by thin-layer chromatography. Secretion of adenylate kinase was minimal when *B. cepacia* cells were grown in PPY broth. However, secretion from the clinical isolates, but not for the environmental isolates, was stimulated in the presence of α2-macroglobulin.

Immunofluorescence microscopy with anti-α2-macroglobulin antibody showed that the clinical isolates had receptors that bound α2-macroglobulin while the environmental isolates lacked such receptors. The clinical and environmental isolates of *B. cepacia* were grown in absence or in presence of 1 mg/ml α2-macroglobulin in PPY broth for 1 hr. Extraneous α2-macroglobulin was removed by washing with phosphate-buffered saline. The cells were incubated for 2 hours with fluorescein isothiocyanate (FITC)-conjugated α2-macroglobulin antibodies, obtained by injecting rabbits with α2-macroglobulin. After washing with phosphate-buffered saline, the FITC conjugated antibody treated cells were fixed in 16% paraformaldehyde, coated on poly-L-lysine coated slides, and examined by confocal microscopy. Only the clinical isolates that showed enhanced cytotoxic factor secretion in the presence of α2-macroglobulin fluoresced (green fluorescing cells), demonstrating the presence of the receptors for α2-macroglobulin.

Example 2. ATP-dependent Macrophage Killing by Filtered Supernatant or Column Chromatographic Fractions Derived from *B. cepacia* Growth Medium A clinical strain of *B. cepacia* (strain 38—collection number 95828, D. G. Allison, University of Manchester Institute of Science and Technology, Manchester, UK) was grown in TB broth (10 g of Bacto tryptone, 3 g of Bacto beef extract per liter of water) at 34° C. on a shaker to an $OD_{550\ nm}$ of 1.3. The growth medium was then centrifuged and the supernatant filtered through a 0.22 μm millipore filter to remove whole cells and debri. Macrophage cells were isolated from J774 cell lines and grown in RPMI medium 1640 (GIBRO-BRL, Grand Island, N.Y.) as described by Zaborina O. et al., Infect. Immun. 67: 5231-5242 (1999). The filtered growth medium was added to hydroxyapatite, ATP-agarose, and Q-sepharose columns in sequence. The flow-through fraction from the hydroxyapatite column (HAFT) was fractionated on the ATP-agarose column (AAFT). The AAFT fraction was then fractionated on the Q-sepharose column (QSFT).

$10^6$ macrophages were added to wells in a 96 well plate and incubated for two hours in a $CO_2$ incubator for attachment. 2 μg of protein from the supernatant or the flow-through fraction from each of the above columns was added to the wells and the plates incubated for 4 hrs in the presence or absence of 1.0 mM ATP. The extent of macrophage cell death was then measured by the release of the intracellular enzyme lactate dehydrogenase (LDH) as described by Zaborina O. et al., Infect. Immun., 67: 5231-5242 (1999). The extent of macrophage killing, in the presence and in the absence of 1.0 mM ATP, by the filtered supernatant (SUP) and the HAFT, AAFT and QSFT column fractions is shown in FIG. 1. All assays were carried out in triplicate and error bars are indicated.

Example 3. ATP-Independent Macrophage Killing by Filtered Supernatant or Column Chromatographic Fractions Derived from *B. cepacia* Growth Medium The supernatant (SUP) and column chromatographic fractions (HAFT, AAFT and QSFT) of *B. cepacia* growth medium were as in Example 2. Macrophage isolation was as in Example 2. The extent of macrophage cell death has been determined by release of LDH as in Example 2 and is shown in FIG. 2. Only the QSFT fraction shows high ATP-independent cytotoxicity towards macrophages.

Example 4. Induction of Apoptosis in Macrophages by *P. aeruginosa* Cytotoxic Factor

*P. aeruginosa* was grown in L broth at 37° C. for 12 hours to an $OD_{550\ nm}$ of 1.2. The growth medium was then centrifuged and the supernatant filtered through a 0.22 μm filter. Supernatant (SUP) and column chromatographic fractions (HAFT, AAFT and QSFT) were collected as in Example 2. Macrophage isolation was as in Example 2. 2 μg of protein from the supernatant or one of the flow-through fractions was added to $1\times10^5$ macrophages in 200 μl of RPMI medium and the mixture incubated overnight. Induction of apoptosis in macrophages either untreated or treated by overnight incubation with the SUP or the HAFT, AAFT or QSFT fractions was measured by confocal microscopy using the ApoAlert Mitochondria Membrane Sensor kit (Clontech Laboratories, Inc., Palo Alto, Calif., U.S.A.) as described by Zaborina O. et al., *Microbiology* 146: 2521-2530 (2000).

In this assay, healthy, non-apoptotic cells fluoresce red while apoptotically dead cells fluoresce green. A combination of red and green produces yellow fluorescing cells, indicating apoptotically dying cells. Nontreated macrophages or macrophages treated overnight with the SUP, HAFT or AAFT fractions fluoresced primarily red, indicating a lack of apoptotic cell death. Macrophages treated overnight with the QSFT fraction fluoresced mostly green, indicating the apoptotic death of most of the macrophages. A time course study showed that apoptosis set in at about 6 hours (indicated by a combination of red and green fluorescence making the cell yellow) and was complete in 12 to 16 hours.

Example 5. Induction of Apoptosis in Mast Cells by *B. cepacia* Cytotoxic Factors Mast cells were isolated by the method described by Melnikov A. et al., Mol. Microbiol. 36: 1481-1493 (2000). *B. cepacia* fractionated growth medium was prepared as in Example 2. Induction of apoptosis in mast cells by *B. cepacia* cytotoxic factor was determined using confocal microscopy, as described in Example 4.

Nontreated mast cells or mast cells, treated overnight with the SUP, HAFT or AAFT fractions of *B. cepacia* growth medium, fluoresced primarily red, indicating a lack of apoptotic cell death. Mast cells treated overnight with the QSFT fraction of *B. cepacia* growth medium fluoresced mostly green, indicating the apoptotic death of most of the mast cells.

Example 6. Induction of Apoptosis in Macrophages by *B. cepacia* and *M. bovis* QSFT Fractions Macrophage isolation was as in Example 2. Induction of apoptosis in macrophages by *B. cepacia* and *M. bovis* cytotoxic factors was determined using the methods of Example 4. Induction of apoptosis of macrophages was observed when they were treated with the *B. cepacia* and *M. bovis* QSFT fractions.

Example 7. Measurement of Caspase Activities (Caspase-3 and Caspase-9) in the Cytosolic Extracts of Macrophages Treated with the *B. cepacia* QSFT Fraction Macrophage isolation was as in Example 2. Macrophages are treated overnight with the *B. cepacia* QSFT fraction using the method described in Example 2. The preparation of macrophage cytoslic extract and the caspase assays were as described by Zaborina O. et al., Microbiology 146: 2521-2530 (2000).

Briefly, determination of caspase-3 activity was performed using Ac-DEVD-pNA (N-acetyl-Asp-Glu-Val-Asp-p-$NO_2$-aniline) as a substrate. Release of pNA (p-nitroaniline) was determined spectrophotometrically at 405 nm from the caspase-3 substrate (200 µm) after 15, 30, 45, 60, 75 and 90 min incubation at 37° C. (FIG. 3A) with uninduced macrophage cytosolic extract; cytosolic extract of macrophages incubated overnight with the *B. cepacia* QSFT fraction (10 µg protein); and cytosolic extract of macrophages incubated overnight with the *B. cepacia* QSFT fraction (10 µg protein) and added inhibitor (DEVD-CHO). 10 µg of macrophage cytosolic protein was used in each case.

In the caspase-9 assay, release of pNA from 200 µM of the caspase-9 substrate Ac-LEHD-pNA (N-acetyl-Leu-Glu-His-Asp-p-$NO_2$-aniline) was determined, after 15, 30, 45, 60, 75 and 90 min incubation (FIG. 3B), with uninduced macrophage cytosolic extract, cytosolic extract of macrophages incubated overnight with the *B. cepacia* QSFT fraction (10 µg protein) and cytosolic extract of macrophages incubated overnight with the *B. cepacia* QSFT fraction (10 µg protein) plus inhibitor (LEHD-CHO). 10 µg of macrophage cytosolic protein was used in each case.

Figure 3A:
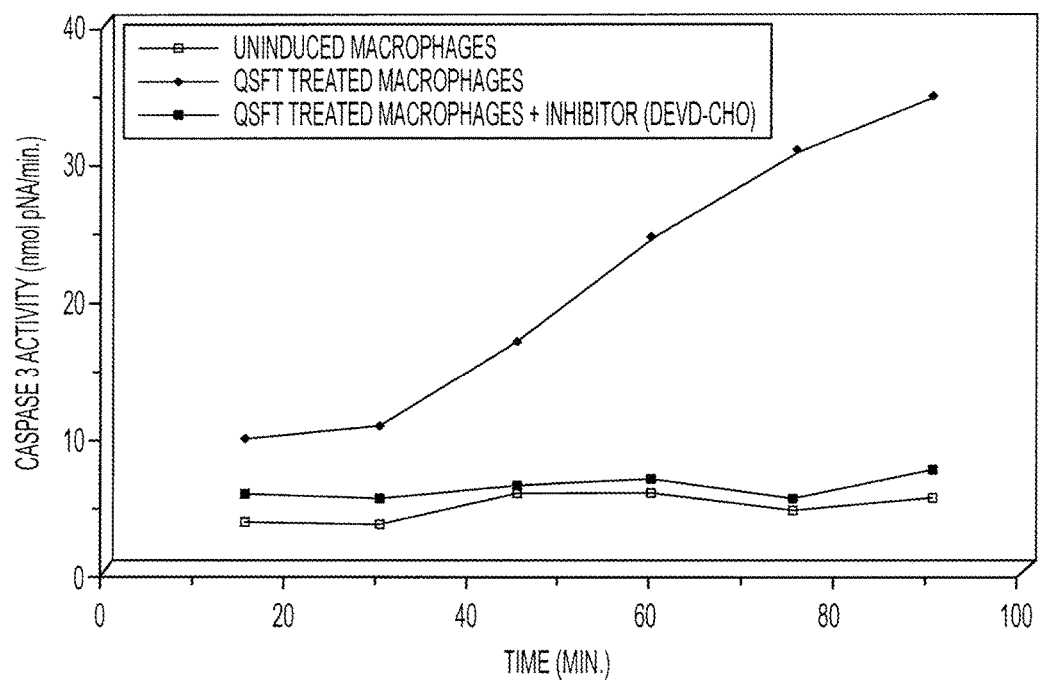
FIG. 3. Graphs showing caspase activities (FIG. 3A-caspase-3.
FIG. 3B-caspase-9) in the cytosolic extracts of J774 macrophages treated with *B. cepacia* QSFT fraction. Cytosolic extracts were prepared from macrophages incubated overnight with *B. cepacia* QSFT fraction (10 μg protein) and from untreated macrophages. The substrate for the determination of caspase-3 activity was Ac-DEVD-pNA (N-acetyl-Asp-Glu-Val-Asp-p-$NO_2$-aniline). The substrate for caspase-9 activity was Ac-LEHD-pNA (N-acetyl-Leu-Glu-His-Asp-p-$NO_2$-aniline). Extracts were incubated with the substrate at 37° C. for the times indicated. 10 μg of macrophage cytosolic protein was used in each case. Release of pNA (p-nitroaniline) was determined spectrophotometrically at 405 nm.
Figure 3B:
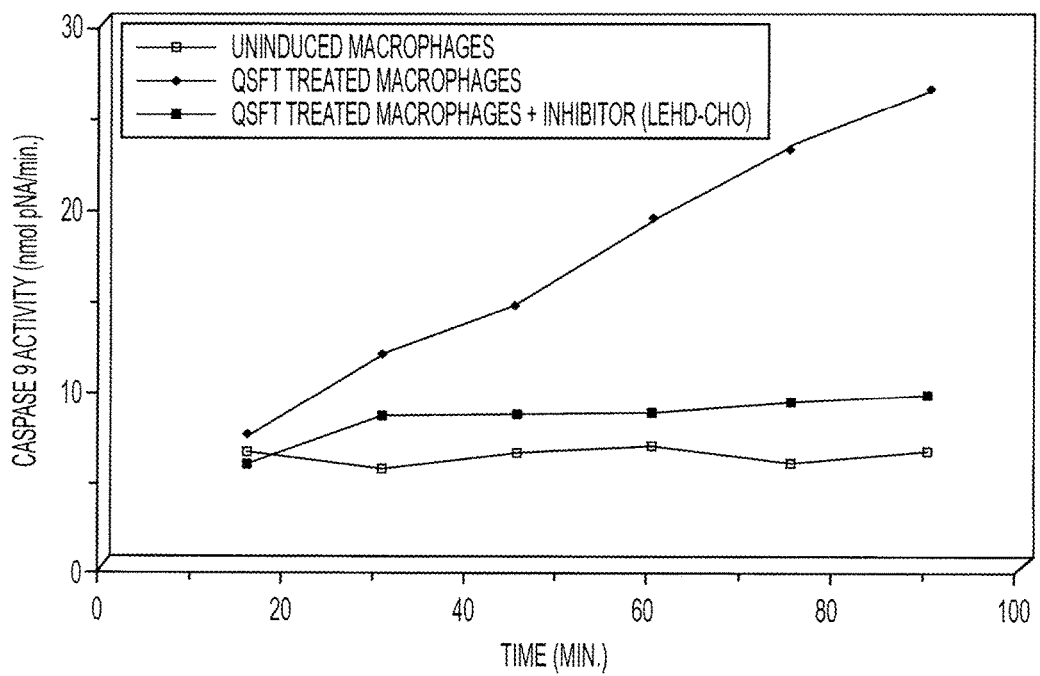

DEVD-CHO and LEHD-CHO respectively block Caspase 3 and Caspase 9 activity and are available from Biomol Research Laboratories, Plymouth Meeting, Pa., U.S.A. The activities of both caspase-9 and caspase-3 increased when macrophages were treated overnight with the *B. cepacia* QSFT fraction (FIGS. 3A and B). These activities remained very low for untreated macrophages or with inhibitor present, suggesting that the induction of apoptosis by the QSFT fractions involves caspase activation.

Example 8. TUNEL Assay to Measure Nuclear DNA Fragmentation in Macrophages Treated with *M. bovis* or *B. cepacia* QSFT Fractions Fractionated *B. cepacia* growth medium was obtained using the method described in Example 2. *M. bovis* BCG was grown in Middlebrook 7H9 broth (Difco Laboratories, Maryland, U.S.A.) supplemented with 2% glycerol, 0.02% TWEEN® 80 and ADC (ablumin/dextrose/citrate) (available from Difco Laboratories, Maryland, U.S.A.). The bacteria were grown for several days at 32° C. on a shaker before harvesting. Fractionated *M. bovis* growth medium was obtained using the method described in Example 2. Macrophage isolation was as in Example 2. Induction of apoptosis in macrophages either untreated or treated by overnight incubation of the SUP or the HAFT, AAFT or QSFT fractions was measured using confocal microscopy by detecting apoptosis-induced nuclear DNA fragmentation with the ApoAlert DNA fragmentation kit (Clontech Laboratories, Inc., Palo Alto, Calif., U.S.A.). This assay is based on terminal deoxynucleotidyltransferase (Tdt)-mediated dUTP nick-end labeling (TUNEL), where Tdt catalyzes the incorporation of fluorescein-dUTP at the free 3'-hydroxyl ends of fragmented DNA in cells undergoing apoptosis. The incorporation of fluorescein-dUTP in the fragmented nuclear DNA generates green fluorescence which is detected by confocal microscopy.

Macrophages treated with either the *M. bovis* or *B. cepacia* QSFT fractions showed a yellow-green nucleus in the red cytoplasmic background, indicating nuclear DNA fragmentation. Little or no fragmentation was observed with untreated macrophages or with macrophages treated with other column fractions.

Example 9. SDS-PAGE Analysis of Proteins in the Supernatant and the AAFT, HAFT and QSFT Fractions of Growth Media from *P. aeruginosa*, *B. cepacia* and *M. bovis*

SDS-PAGE separation showed the proteins present in the supernatant and the AAFT, HAFT and QSFT Fractions of *P. aeruginosa*, *B. cepacia* and *M. bovis*. The QSFT medium fraction from mucoid *P. aeruginosa* strain 8821 showed the presence of two bands, a 18 kDa band corresponding to azurin by N-terminal analysis and a 9 kDa band corresponding to cytochrome $c_{551}$ The *B. cepacia* QSFT fraction showed the presence of three predominant bands of 75 kDa, 20 kDa and 8 kDa. The N-terminal amino acid sequence of 10 amino acids of the 20 kDa band (AHHSVDIQGN), determined by Edman degradation, showed 80% sequence homology to that of the N-terminal 10 amino acid sequence of *P. aeruginosa* azurin while the N-terminal amino acid sequence of 10 amino acids of the 8 kDa band (EDPEV-LFKNK) showed 100% match with that of *P. aeruginosa* cytochrome $c_{551}$. Thus the QSFT fractions having high cytotoxic activity of both *P. aeruginosa* and *B. cepacia* show enrichment with azurin and cytochrome $c_{551}$ type of redox proteins. In contrast, the *M. bovis* QSFT fraction showed a thick 65 kDa band of bovine serum albumin (BSA), which is a constituent of the 7H9 medium used for growing *M. bovis*, as well as several bands of greater than 45 kDa molecular mass, but not the 8 kDa or 22 kDa cytochrome $c_{551}$ or azurin type of proteins.

Figure 4:
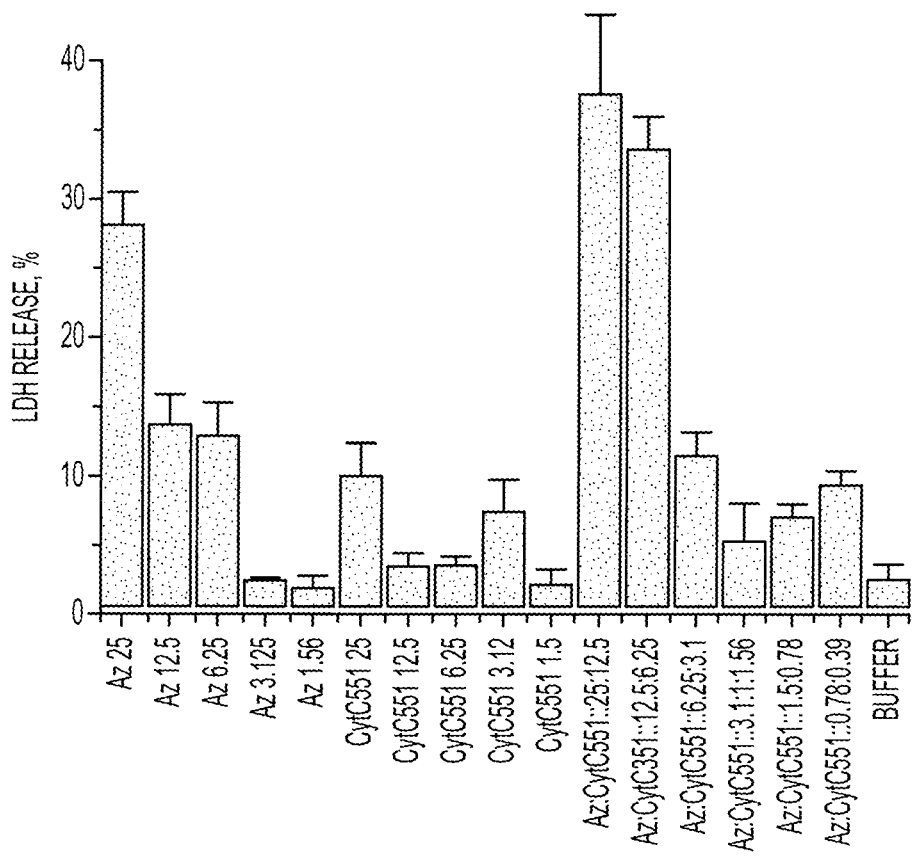
FIG. 4. Chart showing cytotoxicity, as measured by % lactate dehydrogenase (LDH) release, in macrophages in presence of azurin (Az), cytochrome $c_{551}$ (Cyt $C_{551}$) and combination thereof. The numbers represent μg protein. The buffer control (buffer) is shown at right.
Figure 5A:
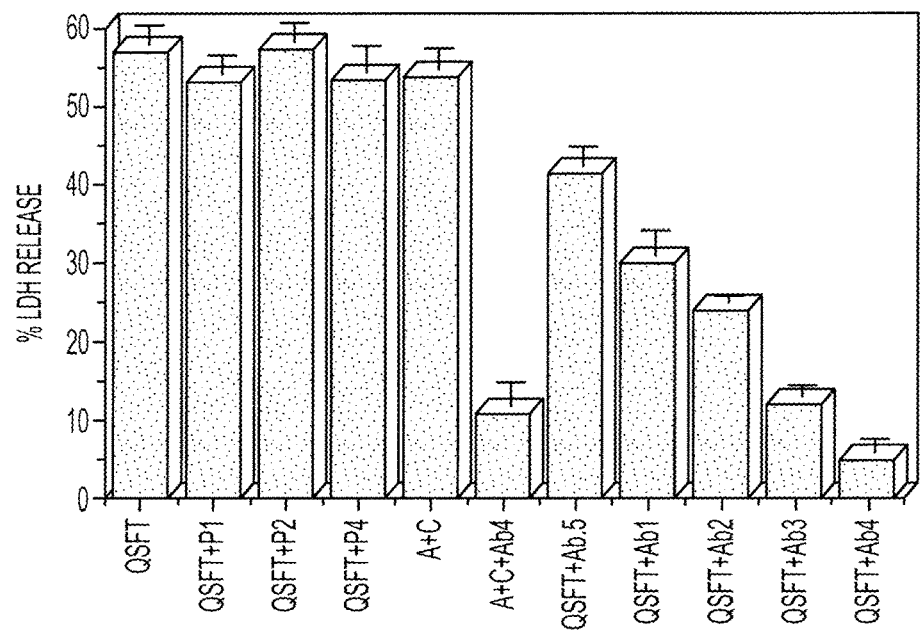
FIG. 5. Chart showing the effects of anti-azurin and anti-cytochrome c551 antibodies on cytotoxicity of *B. cepacia* (A) and *M. bovis* (B) QSFT fractions and in the presence of preimmune serum. A, azurin (50 μg); C, cytochrome c551 (25 μg); ab, combination of anti-azurin and anti-cytochrome c551 antibodies; P, preimmune serum. 2 μg of QSFT fraction were used in each assay. The numbers after ab and P represent μg of the antibody or preimmune protein. Results shown are means±standard deviations of triplicate experiments.
Figure 5B:
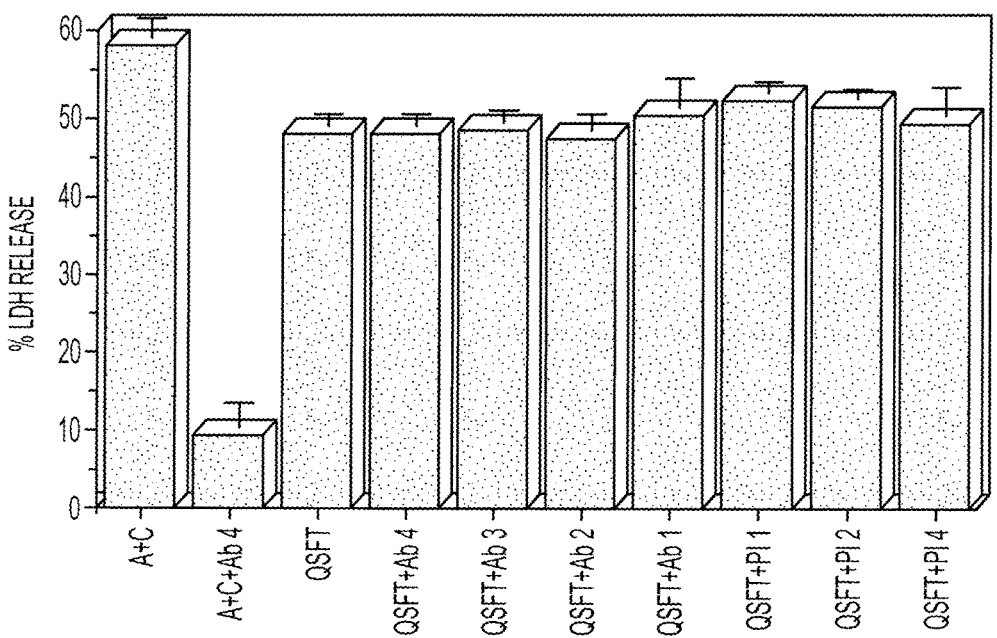
Figure 6:
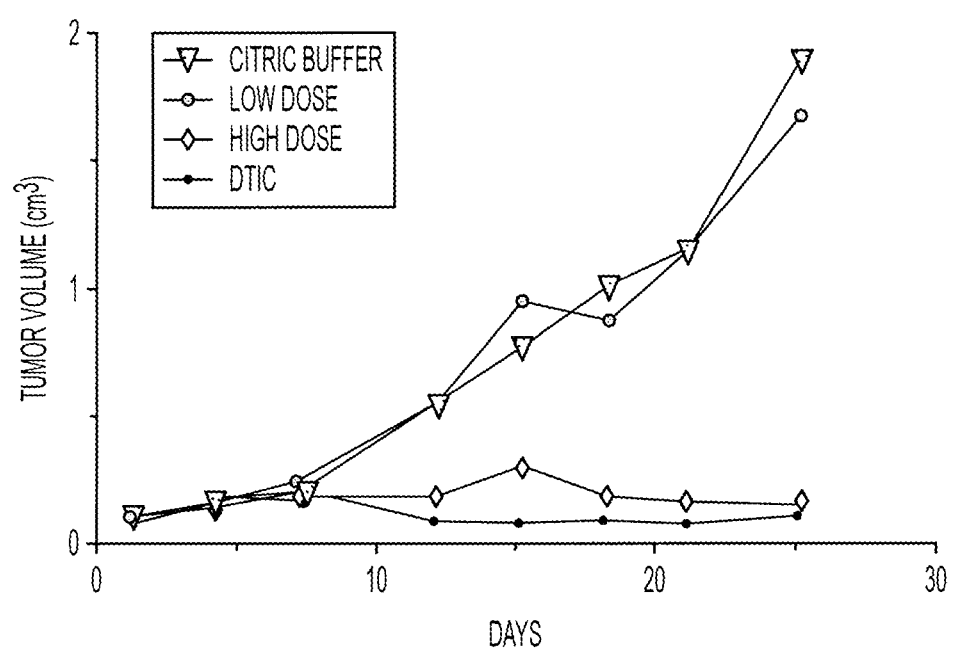
FIG. 6. Graph showing the effect of post injection of azurin/cytochrome $c_{551}$ in nude mice on the size of the tumor after induction of melanoma tumor cells (UISO-Mel-2). Approximately $10^6$ UISO-Mel-2 cells were injected subcutaneously in nude mice followed by once weekly intraperitoneal injections of either citrate buffer (control), a known anti-melanoma drug DTIC (7.5 μg) or three times per week a high (150 μg azurin/75 μg cytochrome $c_{551}$) or low (10 μg azurin/5 μg cytochrome $c_{551}$) dose of azurin/cytochrome $c_{551}$ mixture for 4 weeks. At various times, the sizes (tumor volume) of the tumors in control (buffer treated), DTIC-treated and high and low dose azurin/cytochrome $c_{551}$-treated mice were determined and plotted graphically.
Figure 7:
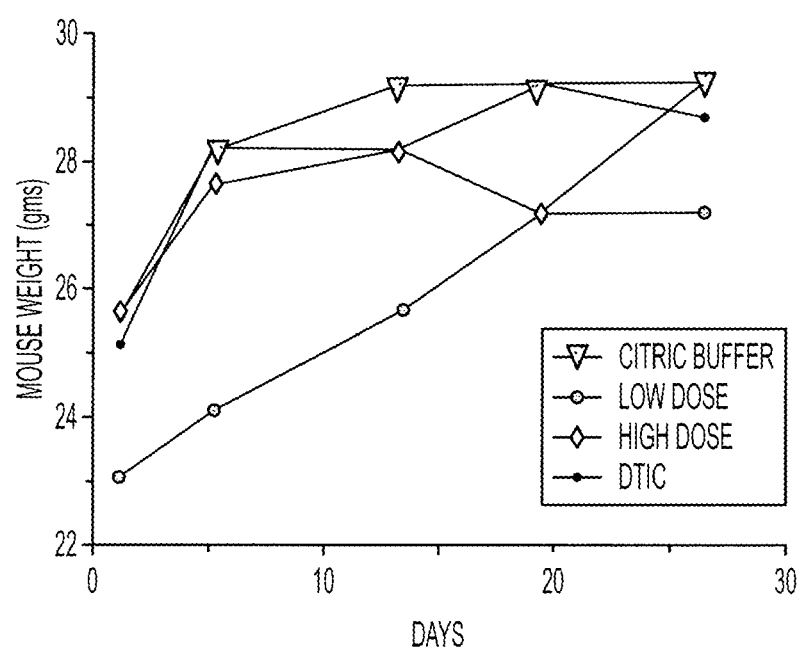
FIG. 7. Graph showing gain or loss of weight of the mice during the experiment described under FIG. 6. During the course of the above experiment, the mice were weighed on a scale and the weights in grams noted.
Figure 8:
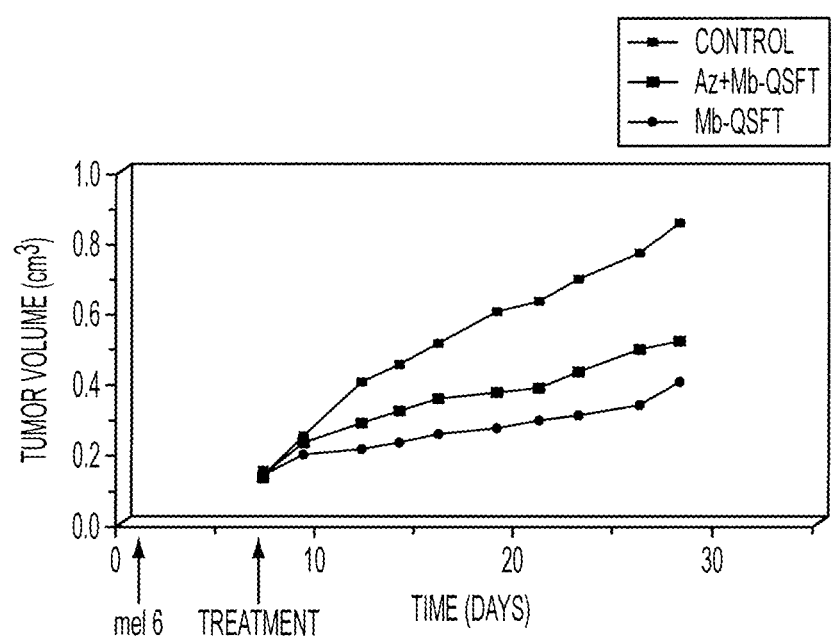
FIG. 8. Graph showing regression of Mel-6 tumor in nude mice treated with *M. bovis* QSFT fraction in the presence or absence of azurin (AZ). Approximately $10^6$ UISO-MeI-6 cells were injected subcutaneously in nude mice. Small tumors developed after approximately one week. The mice were then intraperitonealy injected with phosphate buffered saline (control), *M. bovis* QSFT fraction or a mixture of *M. bovis* QSFT fraction and azurin.

Example 10. Cell Death in Macrophages Treated with Azurin/Cytochrome $C_{551}$ Purified azurin and cytochrome $c_{551}$ (Sigma Chemicals, St. Louis U.S.A.) were added to macrophages, prepared as in Example 2, and the mixture incubated for 2 hrs. Azurin and cytochrome $c_{551}$ concentrations were as in FIG. 4. The numbers represent µg protein. Macrophage cell death was measured by the release of the intracellular enzyme lactate dehydrogenase (LDH) using the method of Example 2. Both azurin and cytochrome $c_{551}$ caused macrophage cell death. A combination of azurin and cytochrome $c_{551}$ caused more extensive macrophage cell death. The buffer control (buffer) is shown at right. (FIG. 4).

Example 11. Induction of Apoptosis in Macrophages Treated with Azurin/Cytochrome $c_{551}$ Macrophage isolation was as in Example 2. The macrophages were treated with azurin/cytochrome $c_{551}$ (50/25 µg) for 4 and 6 hours and then examined by confocal microscopy, using the ApoAlert Mitochondria Membrane Sensor kit as in Example 4, to determine the extent of apoptosis. Macrophages underwent increasing levels of apoptosis with increasing periods of incubation in presence of azurin/cytochrome $c_{551}$ mixture. Control macrophages without treatment (treated with phosphate-buffered saline for 6 hours) did not show apoptosis.

Example 12. Cytotoxicity of an Azurin/Cytochrome $c_{551}$ Mixture or the QSFT Fractions Derived from *B. Cepacia* or *M. bovis* in Macrophages after Pretreatment with Anti-Azurin and Anti-Cytochrome $c_{551}$ Antibodies Macrophage isolation was as in Example 2. Macrophages were treated with a purified azurin/cytochrome $c_{551}$ mixture (50/25 μg), or the *B. cepacia* or *M. bovis* QSFT fractions in the presence and absence of a mixture of anti-azurin and anti-cytochrome $c_{551}$ antibodies prepared in rabbits. Antibodies were mixed in a ratio of 1:1 and the mixed antibody (1, 2, 3, or 4 mg) was used for treatment of macrophages.

The extent of macrophage cell death was determined by release of the LDH as in Example 2. FIG. 5 shows a reduction of cytotoxicity towards macrophages treated with an azurin/cytochrome $c_{551}$ mixture (A+C), or the QSFT fraction derived from *B. cepacia* (Bc-QSFT), when anti-azurin and anti-cytochrome $c_{551}$ antibodies are present. This reduction was not observed with the QSFT fraction from *M. bovis* (Mb-QSFT).

Hence, when an azurin/cytochrome $c_{551}$ mixture or the *B. cepacia* QSFT fraction was treated with a mixture of anti-azurin and anti-cytochrome $c_{551}$ antibodies, and then assayed for macrophage cytotoxicity, the cytotoxicity was greatly diminished. In contrast, when the *M. bovis* QSFT fraction, which was previously shown by SDS-PAGE gel to lack azurin and cytochrome $c_{551}$ bands (Example 9), was pretreated with anti-azurin/anti-cytochrome $c_{551}$ antibodies and then assayed for cytotoxicity, very little reduction in cytotoxicity was observed.

Example 13. Induction of Apoptosis in Tumor Cell Lines by the *B. cepacia* QSFT Fraction and by Azurin/Cytochrome $c_{551}$ as Measured by Confocal Microscopy H460 lung carcinoma, PA-1 ovarian cancer, NCF breast cancer, HT-29 colon cancer and HT-1080 leukemia cell lines were obtained from the American Type Culture Collection (Manassas, Va., U.S.A.). MDD7 and MN1 breast cancer cell lines were obtained from Andrei Gudkov, Ph.D., Cleveland Clinic Foundation (Cleveland, Ohio U.S.A.). UISO-BCA-9 breast cancer and UISO-MEL-1, MEL-2, MEL-6 and MEL-29 melanoma cell lines were developed and maintained as described in Rauth, S et al., In vitro Cellular and Developmental Biology, 30a(2): 79-84 (1994) and Rauth, S et al., Anticancer Research, 14(6): 2457-2463 (1994). Approximately $1\times10^5$ of each cell type were cultured overnight in a 0.15 mm thick dTC3 dish (Bioptech, Butler, Pa., U.S.A.) in the presence of the *B. cepacia* QSFT fraction (5 μg protein) or a azurin/cytochrome $c_{551}$ mixture (50/25 μg). The cells were subsequently examined by confocal microscopy, as in Example 4, to determine the extent of apoptosis. Both the *B. cepacia* QSFT fraction the and azurin/cytochrome $c_{551}$ mixture induced extensive apoptosis in H460 lung carcinoma, HT-29 colon cancer, HT-1080 leukemia, PA-1 ovarian cancer, MDD7, NCF and MN1 breast cancer, and USIO-MEL-1, MEL-2, MEL-6 and MEL-29 melanoma cells after overnight incubation. In each case, cells not treated with cytotoxic factor (phosphate-buffered saline added) did not show extensive apoptosis.

Example 14. Induction of Apoptosis in USIO-MeI-6 Melanoma Cell Line by the *M. bovis* QSFT Fraction as Measured by TUNEL Assay USIO-MeI-6 melanoma cells were prepared as described in Rauth, S et al., Anticancer Research, 14(6): 2457-2463 (1994). *M. bovis* QSFT fraction was prepared as in Example 8. The melanoma cells treated with *M. bovis* QSFT fraction (5 μg protein) and untreated control cells were incubated for 12 hours. Induction of apoptosis was measured using the TUNEL assay to detect apoptosis-induced nuclear DNA fragmentation as in Example 8. Melanoma cells treated with the *M. bovis* QSFT fraction showed a yellow-green nucleus in the red cytoplasmic background, indicating nuclear DNA fragmentation. Little or no fragmentation was observed with untreated melanoma cells.

Example 15. Reduction of Growth of Melanoma Tumor Cells (USIO-MeI-2) in Nude Mice after Treatment with Azurin/Cytochrome $c_{551}$ Approximately $10^6$ USIO-MeI-2 cells were injected subcutaneously in nude mice (available from Frederick Cancer Research and Development Center, Frederick, Md. U.S.A.). Small tumors developed after approximately three weeks. The mice then received once weekly intraperitoneal injections of a known anti-melanoma drug, DTIC [5-(3,3'-N,N-dimethyl triazen-1-yl)-imidazole-4-carboxamide] (7.5 μg) (see Ahlmais et al., Cancer 63: 224-7 (1989)) or three weekly intraperitoneal injections of a high (150 μg azurin/75 μg cytochrome $c_{551}$), low (10 μg azurin/5 μg cytochrome $c_{551}$) dose of azurin/cytochrome $c_{551}$ mixture or control (citrate buffer) for 4 weeks. The tumor volume was determined at intervals in the control, DTIC-treated, and high and low dose azurin/cytochrome $c_{551}$-treated mice.

The increases in tumor size in control, DTIC-treated and azurin/cytochrome $c_{551}$-treated nude mice are shown in FIG. 6 and the weight gain/loss data in such mice are shown in FIG. 7. Post-injection of a high dosage of 150 μg azurin/75 μg cytochrome-$c_{551}$ produced delayed growth and a shrinkage of the tumor size comparable of DTIC. FIG. 7 shows that the injection of either DTIC or azurin/cytochrome $c_{551}$ mixture did not affect the weight gain of the mice. All mice gained weight during the experimental period.

Example 16. Effect of Post Injection of Azurin and *M. bovis* QSFT Fraction in Nude Mice on Tumor Size after Injection of Melanoma Tumor Cells (MeI-6)

Approximately $10^6$ USIO-MeI-6 cells were injected subcutaneously in 3 nude mice (available from Frederick Cancer Research and Development Center, Frederick, Md. U.S.A.). Small tumors developed after approximately three weeks. One mouse was then injected intraperitoneally with phosphate-buffered saline (control), one mouse was injected with *M. bovis* QSFT fraction (5 μg protein) and one mouse was injected with a mixture of *M. bovis* QSFT fraction (5 μg protein) and Azurin (50 μg). The *M. bovis* QSFT fraction was prepared as in Example 8. The sizes (tumor volume) of the tumors in control, *M. bovis* QSFT fraction treated and *M. bovis* QSFT fraction/Azurin treated mice were determined over a period of 30 days. These data are shown in FIG. 8. Both the treated nice showed decreased tumor growth compared to the control mouse.

Example 17. Azurin Induces Apoptosis and Regression of Human Breast Cancer Cells The human breast cell lines MCF-7 (p53+/+) and MDA-MB-157 (p53−/−) were obtained from the stock culture collection of the Department of Surgical Oncology, University of Illinois at Chicago (UIC), Chicago. Normal breast cells (MCF-10F) and skin cells were from the same source. HBL100 cells were a gift from Dr. Nita J. Mahile, Department of Biochemistry and Molecular Biology, Mayo Clinics, Rochester, Minn. The cells were grown either in MEM medium supplemented with Earle's salt, 10% FBS, Penicillin/Streptomycin or Macoy's 5A medium. The cells were grown at 37° C. in 6% $CO_2$.

The azurin-encoding gene of *Pseudomonas aeruginosa* was amplified and cloned in pUC19. Azurin was purified from *E. coli* JM109 as described in Yamada, T. et al., Infect. Immun., vol. 70, pp 7054-62 (2002), the contents of which are incorporated for all purposes by this reference.

Figure 9:
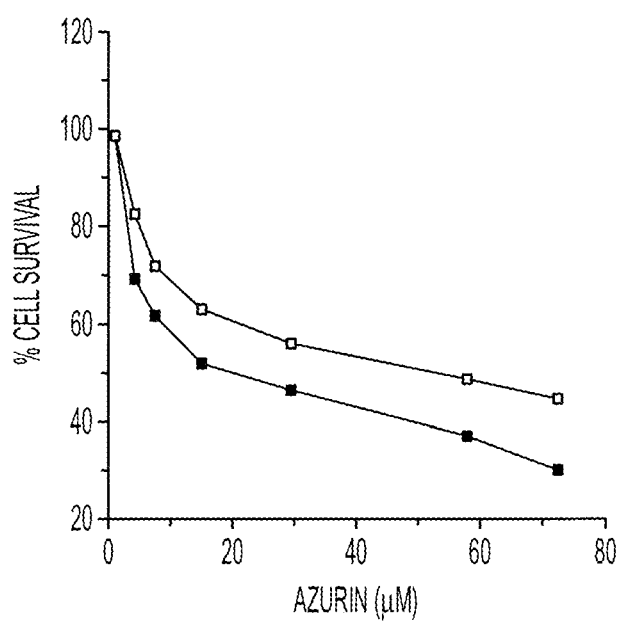
FIG. 9. Graph showing the cytotoxicity of azurin for MCF-7 (■) and MDA-MB-157 (□) cells treated with various concentrations of azurin for 72 hours.

Cytotoxicity of azurin towards cell lines was determined using the MTT assay as described in Yamada et al., (2002). FIG. 9 shows the cytotoxicity of azurin for MCF-7 and MDA-MB-157 cells treated with various concentrations of azurin for 72 hours. After 72 hours of treatment, azurin at a concentration of 28.5 µM (400 µg/ml) induced 50% cell death in MCF-7 cells within 72 hours. Under the same experimental conditions, MDA-MB-157 cells required 57 µM (800 µg/ml) for 50% cell death.

To determine whether azurin induces similar cell death in normal cells, two mammary epithelial cell lines were tested (HBL 100 and MCF-10F). After 72 hours of incubation with 57 µM (800 µg/ml) of azurin, only 20% of MCF-10F cells and 18% of HBL100 cells were nonviable. Cell viability was determined by a cell titer 96 aqueous proteolytic assay (Eilon, G. F. et al., Cancer Chemother. Pharmacol., vol. 45, pp 183-91 (2001) using a kit from Promega (Madison, Wis.).

Example 18. Treatment with Azurin Reduces Tumor Size in Nude Mice Injected with Breast Cancer Tumor Cells Approximately 500,000 MCF-7 cells, obtained as in Example 17, were injected in the right lowest mammary fat pad of estradiol-pretreated female nude mice (available from Frederick Cancer Research and Development Center, Frederick, Md. U.S.A.). The mice were randomized in two groups of 10 mice each. The treated group received 1 mg of azurin in 1 ml of normal saline intraperitoneally daily for 28 days, and the control group received 1 ml of saline daily for 28 days.

The treatment started three days after MCF-7 inoculation. During the course of the experiment, the mice were examined daily, 3-axis tumor volume and body weights were measured twice weekly. On the 29th day, the animals were sacrificed and detailed necropsy was performed. All the tumors and viscera were preserved for histological and immunocytochemical examination.

Tumor volume in the mice treated daily with 1 mg of azurin for 28 days had a substantially slower rate of increase than in the animals in the control group. Univariate analysis of the data showed that the difference in growth rates of the tumor in these two groups (azurin-treated versus control) is significant. For example, 22 days after the start of treatment, the mean tumor volume in treated mice was only 22% of the mean tumor volume for the control mice (i.e., 0.0267 $cm^3$ and 0.1240 $cm^3$ respectively, P=0.0179, Kruskal-Wallis test), demonstrating a 78% tumor growth inhibition.

Figure 10:
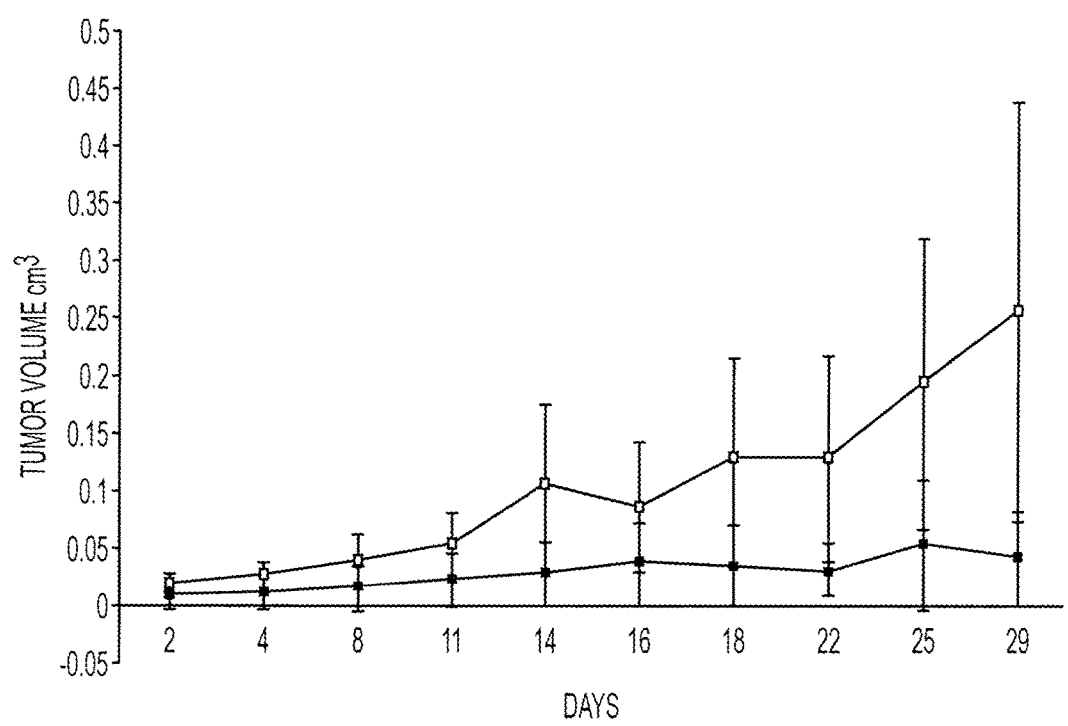
FIG. 10. Graph showing regression of MCF-7 tumor in nude mice treated with azurin (■) and control animals (□).

At the conclusion of the experiment on the $29^{th}$ day, the mean tumor volume in the azurin-treated group was only 15% of the mean tumor volume of the control group. This is further illustrated by FIG. 10 showing the graph of the variation over time of mean tumor volumes for the two groups, expressed in $cm^3$.

In the multivariate approach, nonlinear mixed-effect models were fitted to the data. One model that was fitted for tumor growth was exponential in time, with coefficients that were subject-specific mixed effects. For the control group, the fitted model was: tumor volume=exp {−4.23+0.06*time}, while for the treated group, it was: tumor volume=exp {−4.23+0.03*time}. The difference was statistically significant (P=0.0456). During the period of treatment (28 days), the treated animals did not show any sign of toxicity as evidenced by weight loss and/or other commonly observed signs of toxicity.

The extent of apoptosis in tumors was estimated by TUNEL stain as in Example 8. The azurin-treated group showed a marked increase in apoptotic figures as compared to the controls, where apoptotic cells were rarely encountered.

Example 19. Preparation of Azurin Mutants

Microorganism and Plasmids

The azurin gene (wild type azurin) was amplified by polymerase chain reaction (PCR) according to the method described by Kukimoto et al., FEBS Lett, vol. 394, pp 87-90 (1996), the contents of which are incorporated for all purposes by this reference. PCR was performed using genomic DNA from *P. aeruginosa* strain PAO1 as a template DNA. The forward and reverse primers used were 5'-GCCC<u>AAGCTT</u>ACCTAGGAGGCTGC TCCATGCTA-3' (SEQ ID NO: 8) and 5'-TGAGCCC<u>CTGCAG</u>GCGCCCATGAAAAAGCCCGGC-3' (SEQ ID NO: 9), where the additionally introduced restriction sites of HindIII and PstI sites are underlined.

The amplified DNA fragment of 545 bp, digested with HindIII and PstI, was inserted into the corresponding sites of pUC19 so that the azurin gene was placed downstream of the lac promoter to yield an expression plasmid pUC19-azuA. *E. coli* JM109 was used as a host strain for expression of the azurin gene. The recombinant *E. coli* strain was cultivated in 2YT medium containing 50 µg $ml^{-1}$ ampicillin, 0.1 mM IPTG; and 0.5 mM $CuSO_4$ for 16 h at 37° C. to produce azurin.

Site-Directed Mutagenesis of the Azurin Gene

Site-directed mutagenesis of the azurin gene was performed using a QuickChange site-directed mutagenesis kit (Stratagene, La Jolla, Calif.). A single set of oligonucleotides was designed for each mutation as follows. For C112D: 5'-CAGTACATGTTCTTCGACACCTTCCCGGGCCAC-3' (SEQ ID NO: 10) and 5'-TGGCCCGGGAAGGTGTC-GAAGAACATGTACTGC-3' (SEQ ID NO: 11); for M44K: 5'-CCTGCCGAAGAACGTCAAGGGCCACAACTGGG-3' (SEQ ID NO: 12) and 5'-CCCAGTTGTGGCCCTT-GACGTTCTTCGGCAGG-3'(SEQ ID NO: 13); for M64E: 5'-GGTCACCGACGGCGAGGCTTCCGGCCTGG-3' (SEQ ID NO: 14) and 5'-CCAGGCCGGAAGCCTCGC-CGTCGGTGACC-3'(SEQ ID NO: 15). Mutations were confirmed by DNA sequencing.

Chimeric Mutants of Azurin

Amino acid residues of azurin that were deemed to be candidates for T-cell-epitopes were searched by GENETYX software (Software Development, Tokyo). Seven putative antigenic epitopes, EP1 to EP7, were found as follows: EP1, I20TVDKS[25] (SEQ ID NO: 16); EP2, V49LSTAA[54] (SEQ ID NO: 17); EP3, G58VVT[61] (SEQ ID NO: 18); EP4, G63HASG[66] (SEQ ID NO: 19); EP5, R79VIAH[83] (SEQ ID NO: 20); EP6, K85LIG[88] (SEQ ID NO: 21); and EP7, M121KGTLT[126] (SEQ ID NO: 22).

Figure 11A:
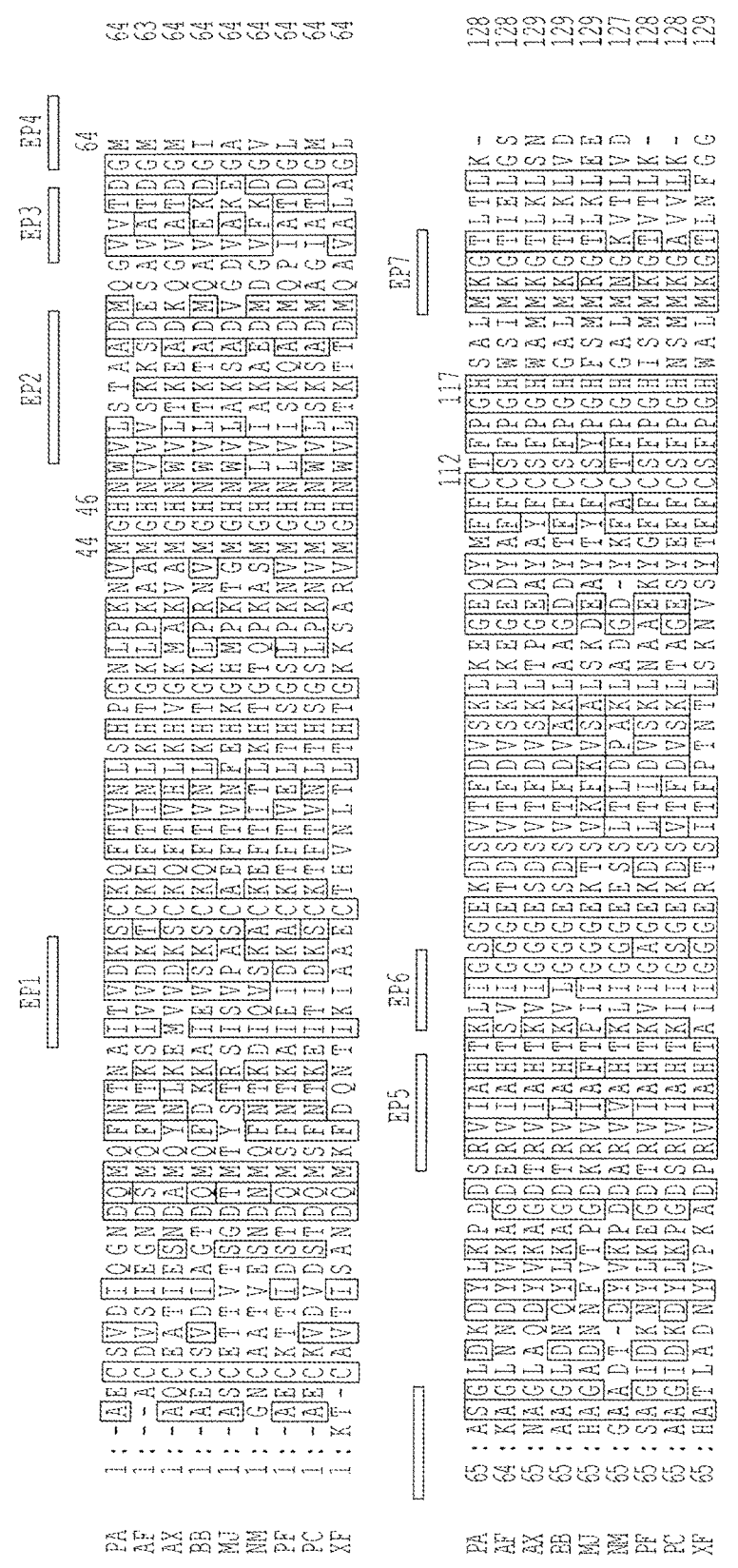

Amino acid sequences of azurins from various microorganisms were obtained from GenBank and aligned by GENETYX software to compare amino acids around the putative T-cell epitope (EP) sites (FIG. 11(a)). EP sites, numbering 1-7, are shown with bars on the top of the sequences. PA, *Pseudomonas aeruginosa* PAO1 (SEQ ID NO: 23); AF, *Alcaligenes faecalis* (SEQ ID NO: 24); AX, *Achromobacter xylosoxidans* ssp. *denitrificans* I (SEQ ID NO: 25); BB, *Bordetella bronchiseptica* (SEQ ID NO: 26); MJ, *Methylomonas* sp. J (SEQ ID NO: 27); NM, *Neisseria meningitidis* Z2491 (SEQ ID NO: 28); PF, *Pseudomonas fiuorescen* (SEQ ID NO: 29); PC, *Pseudomonas chlororaphis* (SEQ ID NO: 30); XE, *Xylella fastidiosa* 9a5c (SEQ ID NO: 31).

The replacements of the amino acids at the putative antigenic epitopes of *P. aeruginosa* with amino acids from other microbial azurins were designed to obtain chimeric azurins in which the antigenic epitopes were altered. The chimeric mutants were constructed cumulatively by site-directed mutagenesis and replacement of a BstEII restriction fragment in the azurin gene using the following oligonucleotides: for T21Qmutation within EP1,5'-CAACACCAAT-GCCATCcagGTCGACAA GAGCTGCAAGC-3' (SEQ ID NO: 32) and 5'-AGCTCTTGTCGACctgGATGGCATTG-GTGT TGAACTGC-3' (SEQ ID NO: 33); for T126K mutation within EP7,5'-GAAGGGCACCCTGAag CTGAAGT-GAT GCGCG-3' (SEQ ID NO: 34), and 5'-GCGCATCACTTCAG ctTCAGGGT GCCCTTCATC-3' (SEQ ID NO: 35); for T52K/A53S mutations within EP2, 5'-AACTGGGTACTGAGCAagtCCGCCGACATGCA-GGGC-3' (SEQ ID NO: 36) and 5'-CTGCATGTCGGCG-GactTGCTCAGTACCCAGTTG TG 3' (SEQ ID NO: 37); for G58P/V591 mutations within EP3,5'-CCGCCGACAT-GCAGccCaTGGTCACC GACGGCATGGC-3' (SEQ ID NO: 38) and 5'-GCCATGCCGTCGGTGACCAtGggCTG-CATGT CGGCGG-3' (SEQ ID NO: 39); for M591/V60A mutations within EP3,5'-CATGCAGCCCA TcGcCAC-CGACGGCATGGC-3' (SEQ ID NO: 40) and 5'-CATGC-CGTCGGTGgCgATGGG CTGCATGTCG-3' (SEQ ID NO: 41); for S66A/G67A/H83F/K85P/L861 mutations within EP4, EP5, and EP6,5'-<u>GTCACC</u>GACGGCATGGCTgC-CGcCCTGGACAAGGATTACCTGAAGCCCG ACGACAGCCGTGTCATCGCCttCACccGaTcATCG-GCTCGGGCGAGAAGG ACTCG-3' (SEQ ID NO: 42) and 5'<u>GTCAC</u>CGAGTCCTTCTCGCCCGAGCCG ATgAtCggGGTGaaGGCGATGACACGGCT-GTCGTCGGGCTTCAGGTAATC CTTGTCCAGGgCG-GcAGCCATGCCGTCG-3' (SEQ ID NO: 43), in which a BstEII site was underlined, were used to replace BstEII fragments from the wt azurin gene. Small letters in the oligonucleotides indicate the mutagenic nucleotides.

Figure 11B:
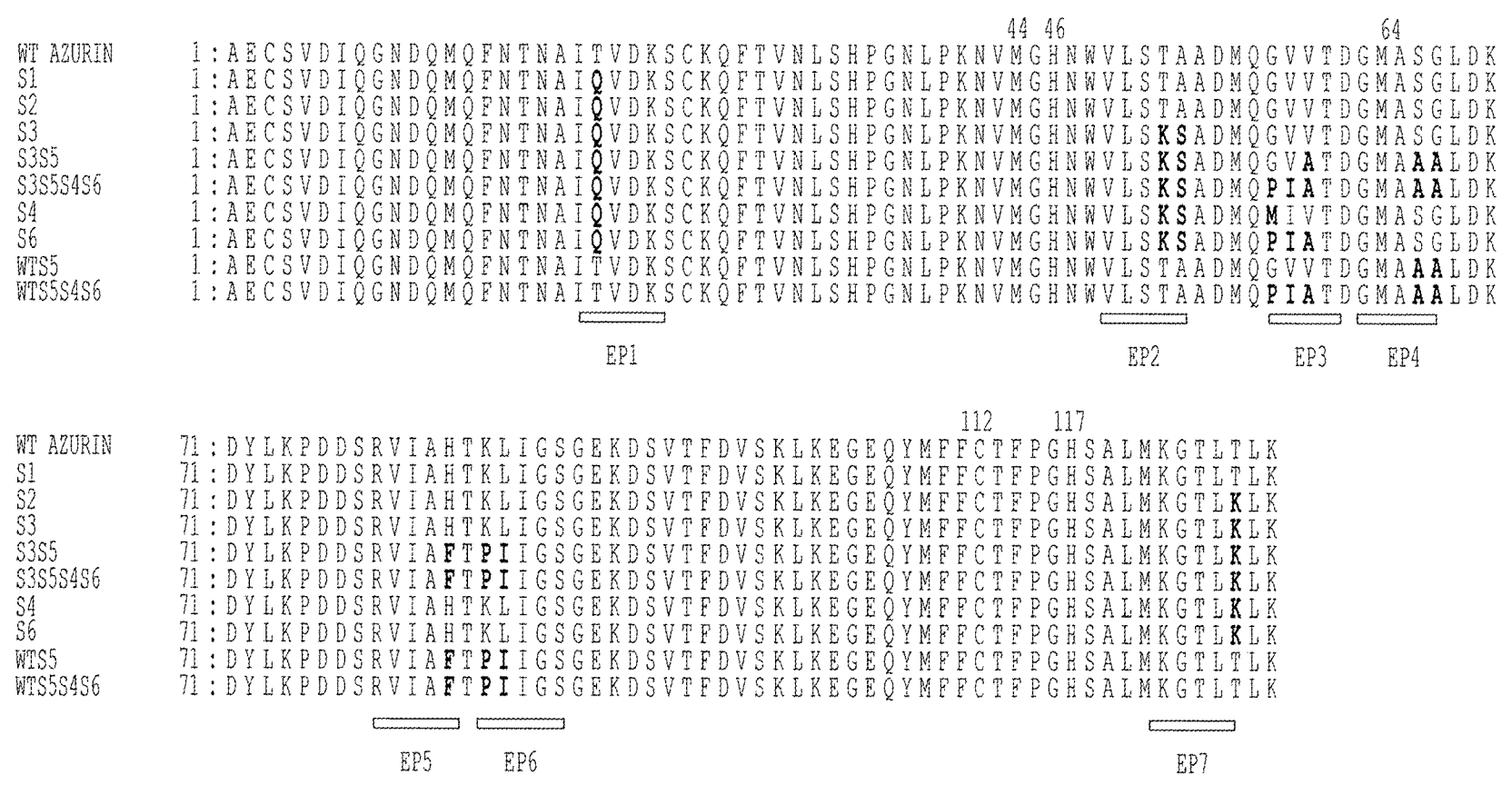

FIG. 11(b) shows wild type azurin and chimeric mutant azurins prepared using the methods described above. 51 (SEQ ID NO. 45), S2 (SEQ ID NO. 46), S3 (SEQ ID NO. 47), S4 (SEQ ID NO. 50), and S6 (SEQ ID NO. 51) were constructed in this order by site-directed mutagenesis cumulatively. WtS5 (SEQ ID NO. 52) and S3S5(SEQ ID NO. 48) were constructed by replacement of the wt (SEQ ID NO. 44) BstEII fragments of wt azurin (wtS5) and S3 azurin (S3S5) with mutagenic BstEII fragment respectively. WtS5S4S6 (SEQ ID NO. 53) and S3S5S4S6 (SEQ ID NO. 49) were constructed by two rounds of site-directed mutagenesis using the wtS5 gene and the S3S5 gene as template DNA respectively. Introduction of mutations was confirmed by DNA sequencing. Replaced amino acids are shown in bold. The genes were expressed in *E. coli* as described for wild type azurin above. No expression of S3S5S4S6 was observed.

Wild type and mutant azurins were purified from periplasmic fractions of recombinant *E. coli* cells using a Q-Sepharose FF column and a Superdex 75 column (Amersham Pharmacia Biotech AB, Uppsala, Sweden) according to the method described by Kukimoto et al. (1996). For the preparation of apo-azurin, wild type azurin was treated with 0.1M MES buffer pH 6.0, containing 0.2M thiourea, 0.25M NaCl and 1 mM EDTA for 16 hr. Released copper was removed by dialysis according to the method described by van Pouderroyen et al., Biochemistry, vol. 35, pp 1397-1407 (1996).

Example 20. Cytotoxic Activity of Azurin and Mutant Azurins

The wide type azurin, apo-azurin, C112D and M44KM64E mutants, and the chimeric mutants prepared in Example 19 were used in macrophage cytotoxicity assays. Macrophage isolation was as in Example 2.

Approximately $1 \times 10^5$ cells per well were seeded into 96-well culture plates in 200 μl of RPMI-1640 medium containing 10% FBS at 37° C. with 5% $CO_2$. After overnight growth, the cells were washed with the same medium, which was thee replaced with new medium containing azurin or mutant azurin. After 24 h treatment 10 μl of 5 mg $mi^4$ M'IT [3-(4 5-dimethylthiazol-2-yl-2,5-diphenyl tetrazolium bromide)] solution was added to the culture and incubated for 2.5 h at 37° C. MTT reaction was terminated by the addition of 40 mM HCl in isopropanol. The MTT formazan formed was measured spectrophotometrically according to the method described by Mosmann, J. Immunol. Methods, vol. 65, pp 55-63 (1983).

Figure 12A:
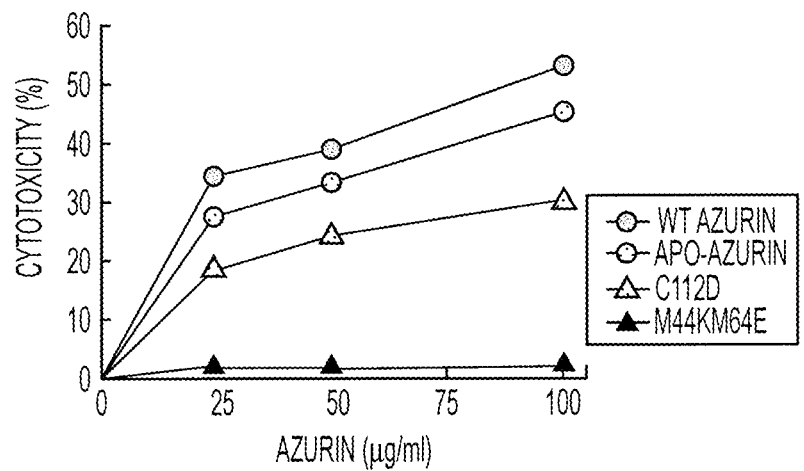
FIGS. 12(a) and 12(b).
Figure 12B:
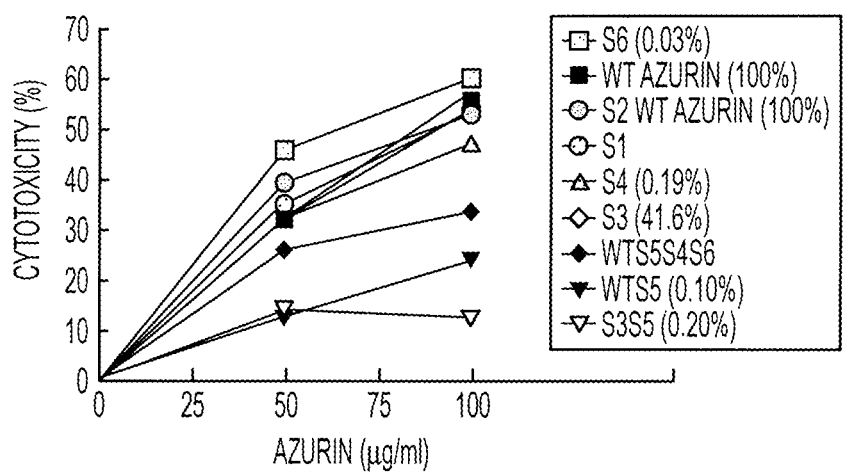

The cytotoxicity of azurin and the mutant azurins is shown in FIGS. 12(a) and 12(b). FIG. 12(b) also shows the relative electron transfer efficiency of the mutants expressed as a percentage of that of wild type azurin. Here, the electron transfer efficiency between oxidized azurin and reduced cytochrome $C_{551}$ was measured by laser flash photolysis as described by Cutruzzola et al., Journal of Inorganic Biochemistry 88; 353-361, 2002.

Example 21. Apoptotic Activity of Azurin and Mutant Azurins

To determine the apoptosis rate induced by wild type azurin or azurin mutants, change in mitochondrial potential was measured by flow cytometry (Becton Dickinson, Inc., Franklin Lakes, N.J.) using an ApoAlert mitochondrial membrane sensor kit (Clontech Laboratories, Inc., Palo Alto, Calif., U.S.A.). Macrophage isolation was as in Example 2.

Approximately $1 \times 10^6$ cells per well were seeded into six-well culture plates in 2 ml of RPMI-1640 medium containing 10% FBS at 37° C. with 5% $CO_2$. After overnight growth, the cells were washed with the same medium, which was thee replaced with new medium containing azurin or mutant azurin. After 16 h treatment, the cells were stained with the MitoSensor dye and analyzed by flow cytometry with a FL-1 filter according to the manufacturer's manuals.

Figure 13:
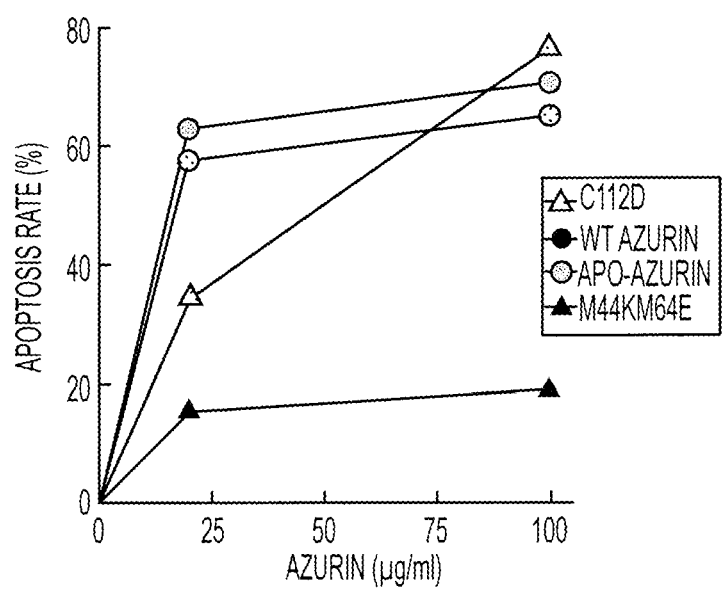
FIG. 13 is a graph showing the apoptotic activity of azurin, apo-azurin, and azurin mutants towards macrophage cells. Wild type azurin (●), apo-azurin (○), M44KM64E (▲), C112D (△).

FIG. 13 shows the apoptotic activity of azurin, apo-azurin, and the C112D and M44KM64E mutants towards macrophage cells. The apoptotic rate (%) is expressed as the fraction of the cell population that shifted from the control population to a green fluorescing apoptotic population.

Example 22. Cytotoxic Activity of Rusticyanin, Apo-Rusticyanin, and Pseudoazurin The wide type azurin was prepared as in Example 19. Rusticyanin from *Thiobacillus ferrooxidans* and pseudoazurin from *Achromobacter cycloclastes* were prepared by hyperexpression of their genes and column chromatographic fractionation as described for azurin (Yamada et al. 2002; Goto et al. 2003). Apo-rusticyanin was prepared using the method described in Example 18. UISO-MeI-2 cells were obtained as in Example 13.

Figure 14:
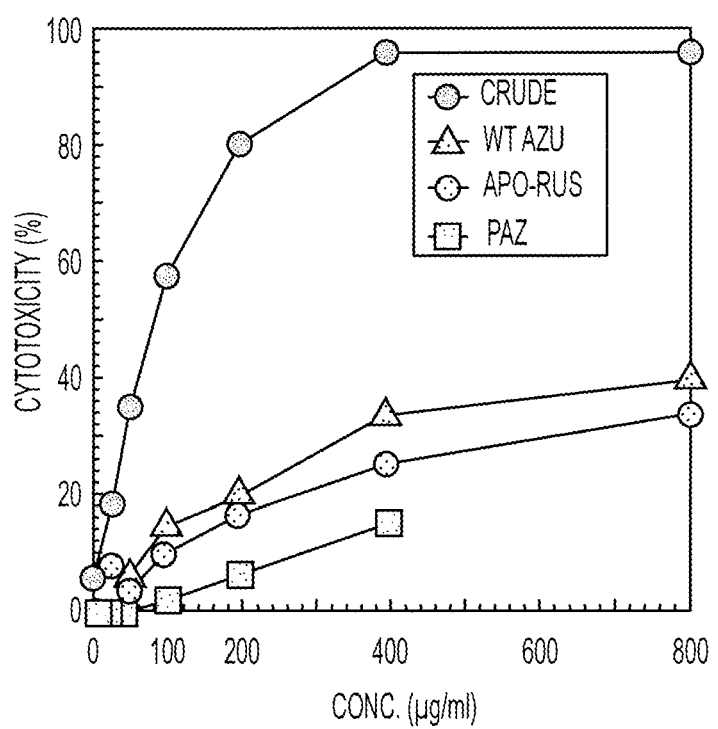
FIG. 14 is a graph showing the cytotoxicity of wild type azurin (wt azu ▲), rusticyanin (crude ●), apo-rusticyanin (apo-rus ○), and pseudoazurin (Paz □).

Approximately $5\times10^3$ cells per well were seeded into 96-well culture plates in 200 µl of MEM medium containing 10% FBS at 37° C. with 5% $CO_2$. After overnight growth, the cells were washed with the same medium, which was then replaced with either buffer (PBS pH 7.4 or Tris-HCl pH 5.0), crude sample containing rusticyanin in Tris-HCl pH5.0, or apo-rusticyanin in PBS pH 7.4. After 24 hr, a MTT assay was performed as described in Example 19. The cytotoxicity of wild type azurin, rusticyanin, apo-rusticyanin and pseudoazurin is shown in FIG. 14.

Example 23. Cytotoxic Activity of Plastocyanin

The wide type azurin was prepared as in Example 18. Plastocyanin from *Phormidium laminosum* was prepared by hyperexpression of its gene and column chromatographic fractionation as described for azurin. Macrophage isolation was as in Example 2.

Figure 15:
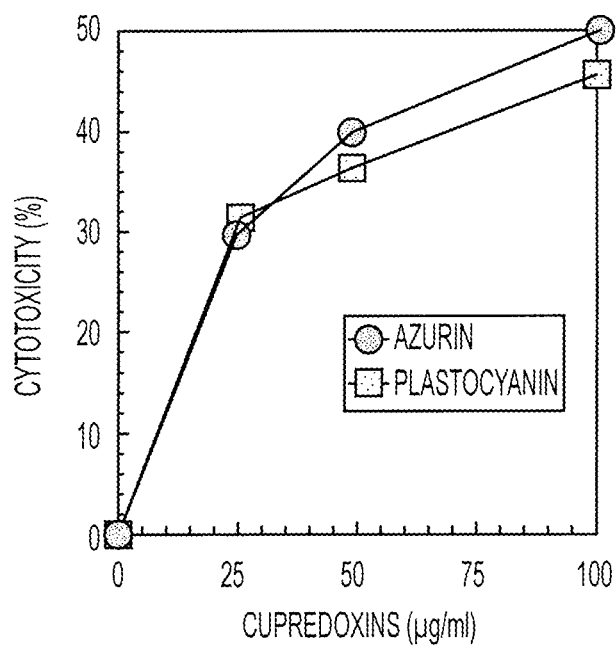
FIG. 15 is a graph showing the cytotoxicity of wild type azurin (●) and plastocyanin (■).

Approximately $1\times10^5$ cells per well were seeded into 96-well culture plates in 200 µl of RPMI-1640 medium containing 10% FBS at 37° C. with 5% $CO_2$. After overnight growth, the cells were washed with the same medium, which was thee replaced with new medium containing azurin or mutant azurin. After 24 hr treatment 10 µl of 5 mg/ml MTT [3-(4 5-dimethylthiazol-2-yl-2,5-diphenyl tetrazolium bromide)] solution was added to the culture and incubated for 2.5 hr at 37° C. MTT reaction was terminated by the addition of 40 mM HCl in isopropanol. The MTT formazan formed was measured spectrophotometrically according to the method described by Mosmann, J. Immunol. Methods, vol. 65, pp 55-63 (1983). The cytotoxicity of wild type azurin and Plastocyanin is shown in FIG. 15.

What is claimed is:

1. A pharmaceutical composition consisting essentially of: a cytochrome $c_{551}$ consisting of SEQ ID NO: 5 and a mutant azurin comprising SEQ ID NO: 6 in a pharmaceutically-acceptable carrier, and wherein the pharmaceutical composition promotes growth arrest in cancer cells and wherein the cytochrome $c_{551}$ is isolated and purified from the species *Pseudomonas aeruginosa*.

2. The pharmaceutical composition of claim 1, wherein the cancer cells are selected from the group consisting of: melanoma cells, leukemia cells, breast cancer cells, ovarian cancer cells, lung cancer cells, mesenchymal cancer cells, colon cancer cells, and aerodigestive tract cancer cells.

3. The pharmaceutical composition of claim 1, wherein the pharmaceutically acceptable carrier is suitable for intravenous administration.

4. The pharmaceutical composition of claim 1, which has low antigenicity.

5. The pharmaceutical composition of claim 1, wherein the pharmaceutically-acceptable carrier is selected from the group consisting of: a tablet, a pill, a dragee, a capsule, a liquid, a gel, a syrup, a slurry, and a suspension.

* * * * *

SEQUENCE LISTING

```
<160> NUMBER OF SEQ ID NOS: 53

<210> SEQ ID NO 1
<211> LENGTH: 128
<212> TYPE: PRT
<213> ORGANISM: Pseudomonas aeruginosa

<400> SEQUENCE: 1

Ala Glu Cys Ser Val Asp Ile Gln Gly Asn Asp Gln Met Gln Phe Asn
1               5                   10                  15

Thr Asn Ala Ile Thr Val Asp Lys Ser Cys Lys Gln Phe Thr Val Asn
            20                  25                  30

Leu Ser His Pro Gly Asn Leu Pro Lys Asn Val Met Gly His Asn Trp
        35                  40                  45

Val Leu Ser Thr Ala Ala Asp Met Gln Gly Val Val Thr Asp Gly Met
    50                  55                  60

Ala Ser Gly Leu Asp Lys Asp Tyr Leu Lys Pro Asp Asp Ser Arg Val
65                  70                  75                  80

Ile Ala His Thr Lys Leu Ile Gly Ser Gly Glu Lys Asp Ser Val Thr
                85                  90                  95

Phe Asp Val Ser Lys Leu Lys Glu Gly Glu Gln Tyr Met Phe Phe Cys
            100                 105                 110

Thr Phe Pro Gly His Ser Ala Leu Met Lys Gly Thr Leu Thr Leu Lys
        115                 120                 125

<210> SEQ ID NO 2
<211> LENGTH: 105
<212> TYPE: PRT
<213> ORGANISM: Phormidium laminosum

<400> SEQUENCE: 2

Glu Thr Phe Thr Val Lys Met Gly Ala Asp Ser Gly Leu Leu Gln Phe
1               5                   10                  15

Glu Pro Ala Asn Val Thr Val His Pro Gly Asp Thr Val Lys Trp Val
            20                  25                  30

Asn Asn Lys Leu Pro Pro His Asn Ile Leu Phe Asp Asp Lys Gln Val
```

```
            35                  40                  45
Pro Gly Ala Ser Lys Glu Leu Ala Asp Lys Leu Ser His Ser Gln Leu
 50                  55                  60
Met Phe Ser Pro Gly Glu Ser Tyr Glu Ile Thr Phe Ser Ser Asp Phe
 65                  70                  75                  80
Pro Ala Gly Thr Tyr Thr Tyr Cys Ala Pro His Arg Gly Ala Gly
                 85                  90                  95
Met Val Gly Lys Ile Thr Val Glu Gly
            100                 105

<210> SEQ ID NO 3
<211> LENGTH: 155
<212> TYPE: PRT
<213> ORGANISM: Thiobacillus ferrooxidans

<400> SEQUENCE: 3

Gly Thr Leu Asp Thr Thr Trp Lys Glu Ala Thr Leu Pro Gln Val Lys
 1               5                  10                  15
Ala Met Leu Glu Lys Asp Thr Gly Lys Val Ser Gly Asp Thr Val Thr
                20                  25                  30
Tyr Ser Gly Lys Thr Val His Val Ala Ala Ala Val Leu Pro Gly
                35                  40                  45
Phe Pro Phe Pro Ser Phe Glu Val His Asp Lys Lys Asn Pro Thr Leu
 50                  55                  60
Glu Ile Pro Ala Gly Ala Thr Val Asp Val Thr Phe Ile Asn Thr Asn
 65                  70                  75                  80
Lys Gly Phe Gly His Ser Phe Asp Ile Thr Lys Lys Gly Pro Pro Tyr
                85                  90                  95
Ala Val Met Pro Val Ile Asp Pro Ile Val Ala Gly Thr Gly Phe Ser
            100                 105                 110
Pro Val Pro Lys Asp Gly Lys Phe Gly Tyr Thr Asp Phe Thr Trp His
            115                 120                 125
Pro Thr Ala Gly Thr Tyr Tyr Tyr Val Cys Gln Ile Pro Gly His Ala
            130                 135                 140
Ala Thr Gly Met Phe Gly Lys Ile Val Val Lys
            145                 150                 155

<210> SEQ ID NO 4
<211> LENGTH: 124
<212> TYPE: PRT
<213> ORGANISM: Achromobacter cycloclastes

<400> SEQUENCE: 4

Ala Asp Phe Glu Val His Met Leu Asn Lys Gly Lys Asp Gly Ala Met
 1               5                  10                  15
Val Phe Glu Pro Ala Ser Leu Lys Val Ala Pro Gly Asp Thr Val Thr
                20                  25                  30
Phe Ile Pro Thr Asp Lys Gly His Asn Val Glu Thr Ile Lys Gly Met
                35                  40                  45
Ile Pro Asp Gly Ala Glu Ala Phe Lys Ser Lys Ile Asn Glu Asn Tyr
 50                  55                  60
Lys Val Thr Phe Thr Ala Pro Gly Val Tyr Gly Val Lys Cys Thr Pro
 65                  70                  75                  80
His Tyr Gly Met Gly Met Val Gly Val Val Gln Val Gly Asp Ala Pro
                85                  90                  95
Ala Asn Leu Glu Ala Val Lys Gly Ala Lys Asn Pro Lys Lys Ala Gln
```

```
                100                 105                 110
Glu Arg Leu Asp Ala Ala Leu Ala Ala Leu Gly Asn
            115                 120

<210> SEQ ID NO 5
<211> LENGTH: 82
<212> TYPE: PRT
<213> ORGANISM: Pseudomonas aeruginosa

<400> SEQUENCE: 5

Glu Asp Pro Glu Val Leu Phe Lys Asn Lys Gly Cys Val Ala Cys His
1               5                   10                  15

Ala Ile Asp Thr Lys Met Val Gly Pro Ala Tyr Lys Asp Val Ala Ala
            20                  25                  30

Lys Phe Ala Gly Gln Ala Gly Ala Glu Ala Glu Leu Ala Gln Arg Ile
        35                  40                  45

Lys Asn Gly Ser Gln Gly Val Trp Gly Pro Ile Pro Met Pro Pro Asn
    50                  55                  60

Ala Val Ser Asp Asp Glu Ala Gln Thr Leu Ala Lys Trp Val Leu Ser
65                  70                  75                  80

Gln Lys

<210> SEQ ID NO 6
<211> LENGTH: 128
<212> TYPE: PRT
<213> ORGANISM: Artificial Sequence
<220> FEATURE:
<223> OTHER INFORMATION: C112D azurin mutant

<400> SEQUENCE: 6

Ala Glu Cys Ser Val Asp Ile Gln Gly Asn Asp Gln Met Gln Phe Asn
1               5                   10                  15

Thr Asn Ala Ile Thr Val Asp Lys Ser Cys Lys Gln Phe Thr Val Asn
            20                  25                  30

Leu Ser His Pro Gly Asn Leu Pro Lys Asn Val Met Gly His Asn Trp
        35                  40                  45

Val Leu Ser Thr Ala Ala Asp Met Gln Gly Val Val Thr Asp Gly Met
    50                  55                  60

Ala Ser Gly Leu Asp Lys Asp Tyr Leu Lys Pro Asp Asp Ser Arg Val
65                  70                  75                  80

Ile Ala His Thr Lys Leu Ile Gly Ser Gly Glu Lys Asp Ser Val Thr
                85                  90                  95

Phe Asp Val Ser Lys Leu Lys Glu Gly Glu Gln Tyr Met Phe Phe Asp
            100                 105                 110

Thr Phe Pro Gly His Ser Ala Leu Met Lys Gly Thr Leu Thr Leu Lys
        115                 120                 125

<210> SEQ ID NO 7
<211> LENGTH: 128
<212> TYPE: PRT
<213> ORGANISM: Artificial Sequence
<220> FEATURE:
<223> OTHER INFORMATION: M44KM64E azurin mutant

<400> SEQUENCE: 7

Ala Glu Cys Ser Val Asp Ile Gln Gly Asn Asp Gln Met Gln Phe Asn
1               5                   10                  15

Thr Asn Ala Ile Thr Val Asp Lys Ser Cys Lys Gln Phe Thr Val Asn
            20                  25                  30
```

```
Leu Ser His Pro Gly Asn Leu Pro Lys Asn Val Lys Gly His Asn Trp
        35                  40                  45

Val Leu Ser Thr Ala Ala Asp Met Gln Gly Val Val Thr Asp Gly Glu
    50                  55                  60

Ala Ser Gly Leu Asp Lys Asp Tyr Leu Lys Pro Asp Asp Ser Arg Val
65                  70                  75                  80

Ile Ala His Thr Lys Leu Ile Gly Ser Gly Glu Lys Asp Ser Val Thr
                85                  90                  95

Phe Asp Val Ser Lys Leu Lys Glu Gly Glu Gln Tyr Met Phe Phe Cys
                100                 105                 110

Thr Phe Pro Gly His Ser Ala Leu Met Lys Gly Thr Leu Thr Leu Lys
                115                 120                 125

<210> SEQ ID NO 8
<211> LENGTH: 33
<212> TYPE: DNA
<213> ORGANISM: Artificial Sequence
<220> FEATURE:
<223> OTHER INFORMATION: Primer

<400> SEQUENCE: 8
gcccaagctt acctaggagg ctgctccatg cta                              33

<210> SEQ ID NO 9
<211> LENGTH: 34
<212> TYPE: DNA
<213> ORGANISM: Artificial Sequence
<220> FEATURE:
<223> OTHER INFORMATION: Primer

<400> SEQUENCE: 9
tgagcccctg caggcgccca tgaaaaagcc cggc                             34

<210> SEQ ID NO 10
<211> LENGTH: 33
<212> TYPE: DNA
<213> ORGANISM: Artificial Sequence
<220> FEATURE:
<223> OTHER INFORMATION: Ofoligonucleotide for C112D mutation

<400> SEQUENCE: 10
cagtacatgt tcttcgacac cttcccgggc cac                              33

<210> SEQ ID NO 11
<211> LENGTH: 33
<212> TYPE: DNA
<213> ORGANISM: Artificial Sequence
<220> FEATURE:
<223> OTHER INFORMATION: Ofoligonucleotide for C112D mutation

<400> SEQUENCE: 11
tggcccggga aggtgtcgaa gaacatgtac tgc                              33

<210> SEQ ID NO 12
<211> LENGTH: 32
<212> TYPE: DNA
<213> ORGANISM: Artificial Sequence
<220> FEATURE:
<223> OTHER INFORMATION: Ofoligonucleotide for M44K mutation

<400> SEQUENCE: 12
cctgccgaag aacgtcaagg gccacaactg gg                               32
```

<210> SEQ ID NO 13
<211> LENGTH: 32
<212> TYPE: DNA
<213> ORGANISM: Artificial Sequence
<220> FEATURE:
<223> OTHER INFORMATION: Ofoligonucleotide for M44K mutation

<400> SEQUENCE: 13
cccagttgtg gcccttgacg ttcttcggca gg                                32

<210> SEQ ID NO 14
<211> LENGTH: 29
<212> TYPE: DNA
<213> ORGANISM: Artificial Sequence
<220> FEATURE:
<223> OTHER INFORMATION: Ofoligonucleotide for M64E mutation

<400> SEQUENCE: 14
ggtcaccgac ggcgaggctt ccggcctgg                                    29

<210> SEQ ID NO 15
<211> LENGTH: 29
<212> TYPE: DNA
<213> ORGANISM: Artificial Sequence
<220> FEATURE:
<223> OTHER INFORMATION: Ofoligonucleotide for M64E mutation

<400> SEQUENCE: 15
ccaggccgga agcctcgccg tcggtgacc                                    29

<210> SEQ ID NO 16
<211> LENGTH: 6
<212> TYPE: PRT
<213> ORGANISM: Artificial Sequence
<220> FEATURE:
<223> OTHER INFORMATION: Antigenic epitope, EP1

<400> SEQUENCE: 16

Ile Thr Val Asp Lys Ser
1               5

<210> SEQ ID NO 17
<211> LENGTH: 6
<212> TYPE: PRT
<213> ORGANISM: Artificial Sequence
<220> FEATURE:
<223> OTHER INFORMATION: Antigenic epitope, EP2

<400> SEQUENCE: 17

Val Leu Ser Thr Ala Ala
1               5

<210> SEQ ID NO 18
<211> LENGTH: 4
<212> TYPE: PRT
<213> ORGANISM: Artificial Sequence
<220> FEATURE:
<223> OTHER INFORMATION: Antigenic Epitope, EP3

<400> SEQUENCE: 18

Gly Val Val Thr
1

<210> SEQ ID NO 19
<211> LENGTH: 5
<212> TYPE: PRT

-continued

<213> ORGANISM: Artificial Sequence
<220> FEATURE:
<223> OTHER INFORMATION: Antigenic epitope, EP4

<400> SEQUENCE: 19

Gly Met Ala Ser Gly
1               5

<210> SEQ ID NO 20
<211> LENGTH: 5
<212> TYPE: PRT
<213> ORGANISM: Artificial Sequence
<220> FEATURE:
<223> OTHER INFORMATION: Antigenic epitope, EP5

<400> SEQUENCE: 20

Arg Val Ile Ala His
1               5

<210> SEQ ID NO 21
<211> LENGTH: 4
<212> TYPE: PRT
<213> ORGANISM: Artificial Sequence
<220> FEATURE:
<223> OTHER INFORMATION: Antigenic epitope, EP6

<400> SEQUENCE: 21

Lys Leu Ile Gly
1

<210> SEQ ID NO 22
<211> LENGTH: 6
<212> TYPE: PRT
<213> ORGANISM: Artificial Sequence
<220> FEATURE:
<223> OTHER INFORMATION: Antigenic epitope, EP7

<400> SEQUENCE: 22

Met Lys Gly Thr Leu Thr
1               5

<210> SEQ ID NO 23
<211> LENGTH: 128
<212> TYPE: PRT
<213> ORGANISM: Pseudomonas aeruginosa

<400> SEQUENCE: 23

Ala Glu Cys Ser Val Asp Ile Gln Gly Asn Asp Gln Met Gln Phe Asn
1               5                   10                  15

Thr Asn Ala Ile Thr Val Asp Lys Ser Cys Lys Gln Phe Thr Val Asn
                20                  25                  30

Leu Ser His Pro Gly Asn Leu Pro Lys Asn Val Met Gly His Asn Trp
            35                  40                  45

Val Leu Ser Thr Ala Ala Asp Met Gln Gly Val Val Thr Asp Gly Met
        50                  55                  60

Ala Ser Gly Leu Asp Lys Asp Tyr Leu Lys Pro Asp Asp Ser Arg Val
65                  70                  75                  80

Ile Ala His Thr Lys Leu Ile Gly Ser Gly Glu Lys Asp Ser Val Thr
                85                  90                  95

Phe Asp Val Ser Lys Leu Lys Glu Gly Glu Gln Tyr Met Phe Phe Cys
                100                 105                 110

Thr Phe Pro Gly His Ser Ala Leu Met Lys Gly Thr Leu Thr Leu Lys
            115                 120                 125

<210> SEQ ID NO 24
<211> LENGTH: 128
<212> TYPE: PRT
<213> ORGANISM: Alcaligenes faecalis

<400> SEQUENCE: 24

Ala Cys Asp Val Ser Ile Glu Gly Asn Asp Ser Met Gln Phe Asn Thr
1               5                   10                  15

Lys Ser Ile Val Val Asp Lys Thr Cys Lys Glu Phe Thr Ile Asn Leu
            20                  25                  30

Lys His Thr Gly Lys Leu Pro Lys Ala Ala Met Gly His Asn Val Val
        35                  40                  45

Val Ser Lys Lys Ser Asp Glu Ser Ala Val Ala Thr Asp Gly Met Lys
    50                  55                  60

Ala Gly Leu Asn Asn Asp Tyr Val Lys Ala Gly Asp Glu Arg Val Ile
65                  70                  75                  80

Ala His Thr Ser Val Ile Gly Gly Gly Glu Thr Asp Ser Val Thr Phe
                85                  90                  95

Asp Val Ser Lys Leu Lys Glu Gly Glu Asp Tyr Ala Phe Phe Cys Ser
            100                 105                 110

Phe Pro Gly His Trp Ser Ile Met Lys Gly Thr Ile Glu Leu Gly Ser
        115                 120                 125

<210> SEQ ID NO 25
<211> LENGTH: 129
<212> TYPE: PRT
<213> ORGANISM: Achromobacter xylosoxidans ssp. denitrificans

<400> SEQUENCE: 25

Ala Gln Cys Glu Ala Thr Ile Glu Ser Asn Asp Ala Met Gln Tyr Asn
1               5                   10                  15

Leu Lys Glu Met Val Val Asp Lys Ser Cys Lys Gln Phe Thr Val His
            20                  25                  30

Leu Lys His Val Gly Lys Met Ala Lys Val Ala Met Gly His Asn Trp
        35                  40                  45

Val Leu Thr Lys Glu Ala Asp Lys Gln Gly Val Ala Thr Asp Gly Met
    50                  55                  60

Asn Ala Gly Leu Ala Gln Asp Tyr Val Lys Ala Gly Asp Thr Arg Val
65                  70                  75                  80

Ile Ala His Thr Lys Val Ile Gly Gly Gly Glu Ser Asp Ser Val Thr
                85                  90                  95

Phe Asp Val Ser Lys Leu Thr Pro Gly Glu Ala Tyr Ala Tyr Phe Cys
            100                 105                 110

Ser Phe Pro Gly His Trp Ala Met Met Lys Gly Thr Leu Lys Leu Ser
        115                 120                 125

Asn

<210> SEQ ID NO 26
<211> LENGTH: 129
<212> TYPE: PRT
<213> ORGANISM: Bordetella bronchiseptica

<400> SEQUENCE: 26

Ala Glu Cys Ser Val Asp Ile Ala Gly Thr Asp Gln Met Gln Phe Asp
1               5                   10                  15

Lys Lys Ala Ile Glu Val Ser Lys Ser Cys Lys Gln Phe Thr Val Asn

-continued

```
                 20                  25                  30
Leu Lys His Thr Gly Lys Leu Pro Arg Asn Val Met Gly His Asn Trp
             35                  40                  45
Val Leu Thr Lys Thr Ala Asp Met Gln Ala Val Glu Lys Asp Gly Ile
 50                  55                  60
Ala Ala Gly Leu Asp Asn Gln Tyr Leu Lys Ala Gly Asp Thr Arg Val
 65                  70                  75                  80
Leu Ala His Thr Lys Val Leu Gly Gly Gly Glu Ser Asp Ser Val Thr
                 85                  90                  95
Phe Asp Val Ala Lys Leu Ala Ala Gly Asp Asp Tyr Thr Phe Phe Cys
                100                 105                 110
Ser Phe Pro Gly His Gly Ala Leu Met Lys Gly Thr Leu Lys Leu Val
                115                 120                 125
Asp

<210> SEQ ID NO 27
<211> LENGTH: 129
<212> TYPE: PRT
<213> ORGANISM: Methylomonas sp. J

<400> SEQUENCE: 27

Ala Ser Cys Glu Thr Thr Val Thr Ser Gly Asp Thr Met Thr Tyr Ser
  1                   5                  10                  15
Thr Arg Ser Ile Ser Val Pro Ala Ser Cys Ala Glu Phe Thr Val Asn
                 20                  25                  30
Phe Glu His Lys Gly His Met Pro Lys Thr Gly Met Gly His Asn Trp
             35                  40                  45
Val Leu Ala Lys Ser Ala Asp Val Gly Asp Val Ala Lys Glu Gly Ala
 50                  55                  60
His Ala Gly Ala Asp Asn Asn Phe Val Thr Pro Gly Asp Lys Arg Val
 65                  70                  75                  80
Ile Ala Phe Thr Pro Ile Ile Gly Gly Gly Lys Thr Ser Val Lys
                 85                  90                  95
Phe Lys Val Ser Ala Leu Ser Lys Asp Glu Ala Tyr Thr Tyr Phe Cys
                100                 105                 110
Ser Tyr Pro Gly His Phe Ser Met Met Arg Gly Thr Leu Lys Leu Glu
                115                 120                 125
Glu

<210> SEQ ID NO 28
<211> LENGTH: 166
<212> TYPE: PRT
<213> ORGANISM: Neisseria meningitidis

<400> SEQUENCE: 28

Cys Ser Gln Glu Pro Ala Ala Pro Ala Ala Glu Ala Thr Pro Ala Ala
  1                   5                  10                  15
Glu Ala Pro Ala Ser Glu Ala Pro Ala Ala Glu Ala Ala Pro Ala Asp
                 20                  25                  30
Ala Ala Glu Ala Pro Ala Ala Gly Asn Cys Ala Ala Thr Val Glu Ser
             35                  40                  45
Asn Asp Asn Met Gln Phe Asn Thr Lys Asp Ile Gln Val Ser Lys Ala
 50                  55                  60
Cys Lys Glu Phe Thr Ile Thr Leu Lys His Thr Gly Thr Gln Pro Lys
 65                  70                  75                  80
```

```
Thr Ser Met Gly His Asn Ile Val Ile Gly Lys Thr Glu Asp Met Asp
                    85                  90                  95

Gly Ile Phe Lys Asp Gly Val Gly Ala Ala Asp Thr Asp Tyr Val Lys
            100                 105                 110

Pro Asp Asp Ala Arg Val Val Ala His Thr Lys Leu Ile Gly Gly Gly
        115                 120                 125

Glu Glu Ser Ser Leu Thr Leu Asp Pro Ala Lys Leu Ala Asp Gly Glu
130                 135                 140

Tyr Lys Phe Ala Cys Thr Phe Pro Gly His Gly Ala Leu Met Asn Gly
145                 150                 155                 160

Lys Val Thr Leu Val Asp
                165
```

```
<210> SEQ ID NO 29
<211> LENGTH: 128
<212> TYPE: PRT
<213> ORGANISM: Pseudomonas fluorescens

<400> SEQUENCE: 29

Ala Glu Cys Lys Thr Thr Ile Asp Ser Thr Asp Gln Met Ser Phe Asn
1               5                   10                  15

Thr Lys Ala Ile Glu Ile Asp Lys Ala Cys Lys Thr Phe Thr Val Glu
            20                  25                  30

Leu Thr His Ser Gly Ser Leu Pro Lys Asn Val Met Gly His Asn Leu
        35                  40                  45

Val Ile Ser Lys Gln Ala Asp Met Gln Pro Ile Ala Thr Asp Gly Leu
    50                  55                  60

Ser Ala Gly Ile Asp Lys Asn Tyr Leu Lys Glu Gly Asp Thr Arg Val
65                  70                  75                  80

Ile Ala His Thr Lys Val Ile Gly Ala Gly Glu Lys Asp Ser Leu Thr
                85                  90                  95

Ile Asp Val Ser Lys Leu Asn Ala Ala Glu Lys Tyr Gly Phe Phe Cys
            100                 105                 110

Ser Phe Pro Gly His Ile Ser Met Met Lys Gly Thr Val Thr Leu Lys
        115                 120                 125
```

```
<210> SEQ ID NO 30
<211> LENGTH: 128
<212> TYPE: PRT
<213> ORGANISM: Pseudomonas chlororaphis

<400> SEQUENCE: 30

Ala Glu Cys Lys Val Asp Val Asp Ser Thr Asp Gln Met Ser Phe Asn
1               5                   10                  15

Thr Lys Glu Ile Thr Ile Asp Lys Ser Cys Lys Thr Phe Thr Val Asn
            20                  25                  30

Leu Thr His Ser Gly Ser Leu Pro Lys Asn Val Met Gly His Asn Trp
        35                  40                  45

Val Leu Ser Lys Ser Ala Asp Met Ala Gly Ile Ala Thr Asp Gly Met
    50                  55                  60

Ala Ala Gly Ile Asp Lys Asp Tyr Leu Lys Pro Gly Asp Ser Arg Val
65                  70                  75                  80

Ile Ala His Thr Lys Ile Ile Gly Ser Gly Glu Lys Asp Ser Val Thr
                85                  90                  95

Phe Asp Val Ser Lys Leu Thr Ala Gly Glu Ser Tyr Gly Phe Phe Cys
            100                 105                 110
```

-continued

```
Ser Phe Pro Gly His Asn Ser Met Met Lys Gly Ala Val Val Leu Lys
        115                 120                 125

<210> SEQ ID NO 31
<211> LENGTH: 129
<212> TYPE: PRT
<213> ORGANISM: Xylella fastidiosa 9a5c

<400> SEQUENCE: 31

Lys Thr Cys Ala Val Thr Ile Ser Ala Asn Asp Gln Met Lys Phe Asp
1               5                   10                  15

Gln Asn Thr Ile Lys Ile Ala Ala Glu Cys Thr His Val Asn Leu Thr
            20                  25                  30

Leu Thr His Thr Gly Lys Lys Ser Ala Arg Val Met Gly His Asn Trp
        35                  40                  45

Val Leu Thr Lys Thr Thr Asp Met Gln Ala Val Ala Leu Ala Gly Leu
    50                  55                  60

His Ala Thr Leu Ala Asp Asn Tyr Val Pro Lys Ala Asp Pro Arg Val
65                  70                  75                  80

Ile Ala His Thr Ala Ile Ile Gly Gly Gly Glu Arg Thr Ser Ile Thr
                85                  90                  95

Phe Pro Thr Asn Thr Leu Ser Lys Asn Val Ser Tyr Thr Phe Phe Cys
            100                 105                 110

Ser Phe Pro Gly His Trp Ala Leu Met Lys Gly Thr Leu Asn Phe Gly
        115                 120                 125

Gly

<210> SEQ ID NO 32
<211> LENGTH: 38
<212> TYPE: DNA
<213> ORGANISM: Artificial Sequence
<220> FEATURE:
<223> OTHER INFORMATION: Oligonucleotide for T21Q mutation within EP1

<400> SEQUENCE: 32
caacaccaat gccatccagg tcgacaagag ctgcaagc                              38

<210> SEQ ID NO 33
<211> LENGTH: 38
<212> TYPE: DNA
<213> ORGANISM: Artificial Sequence
<220> FEATURE:
<223> OTHER INFORMATION: Oligonucleotide for T21Q mutation within EP1

<400> SEQUENCE: 33
agctcttgtc gacctggatg gcattggtgt tgaactgc                              38

<210> SEQ ID NO 34
<211> LENGTH: 31
<212> TYPE: DNA
<213> ORGANISM: Artificial Sequence
<220> FEATURE:
<223> OTHER INFORMATION: Oligonucleotide for T126K mutation within EP7

<400> SEQUENCE: 34
gaagggcacc ctgaagctga agtgatgcgc g                                     31

<210> SEQ ID NO 35
<211> LENGTH: 33
<212> TYPE: DNA
<213> ORGANISM: Artificial Sequence
<220> FEATURE:
```

<223> OTHER INFORMATION: Oligonucleotide for T126K mutation within EP7

<400> SEQUENCE: 35
gcgcatcact tcagcttcag ggtgcccttc atc    33

<210> SEQ ID NO 36
<211> LENGTH: 36
<212> TYPE: DNA
<213> ORGANISM: Artificial sequence
<220> FEATURE:
<223> OTHER INFORMATION: Oligonucleotide for T52K/A53S mutations within EP2

<400> SEQUENCE: 36
aactgggtac tgagcaagtc cgccgacatg cagggc    36

<210> SEQ ID NO 37
<211> LENGTH: 36
<212> TYPE: DNA
<213> ORGANISM: Artificial Sequence
<220> FEATURE:
<223> OTHER INFORMATION: Oligonucleotide for T52K/A53S mutations within EP2

<400> SEQUENCE: 37
ctgcatgtcg gcggacttgc tcagtaccca gttgtg    36

<210> SEQ ID NO 38
<211> LENGTH: 37
<212> TYPE: DNA
<213> ORGANISM: Artificial Sequence
<220> FEATURE:
<223> OTHER INFORMATION: Oligonucleotide for G58P/V59I mutations within EP3

<400> SEQUENCE: 38
ccgccgacat gcagcccatg gtcaccgacg gcatggc    37

<210> SEQ ID NO 39
<211> LENGTH: 37
<212> TYPE: DNA
<213> ORGANISM: Artificial Sequence
<220> FEATURE:
<223> OTHER INFORMATION: Oligonucleotide for G58P/V59I mutations within EP3

<400> SEQUENCE: 39
gccatgccgt cggtgaccat gggctgcatg tcggcgg    37

<210> SEQ ID NO 40
<211> LENGTH: 30
<212> TYPE: DNA
<213> ORGANISM: Artificial Sequence
<220> FEATURE:
<223> OTHER INFORMATION: Oligonucleotide for M59I/V60A mutations within EP3

<400> SEQUENCE: 40
catgcagccc atcgccaccg acggcatggc    30

<210> SEQ ID NO 41
<211> LENGTH: 31
<212> TYPE: DNA
<213> ORGANISM: Artificial Sequence
<220> FEATURE:
<223> OTHER INFORMATION: Oligonucleotide for M59I/V60A mutations within EP3

<400> SEQUENCE: 41
catgccgtcg gtggcgatgg gctgcatgtc g                                      31

<210> SEQ ID NO 42
<211> LENGTH: 104
<212> TYPE: DNA
<213> ORGANISM: Artificial Sequence
<220> FEATURE:
<223> OTHER INFORMATION: Oligonucleotide for S66A/G67A/H83F/K85P/L86I
      mutations within EP4, EP5, and EP6

<400> SEQUENCE: 42
gtcaccgacg gcatggctgc cgccctggac aaggattacc tgaagcccga cgacagccgt      60
gtcatcgcct tcacccgatc atcggctcgg gcgagaagga ctcg                      104

<210> SEQ ID NO 43
<211> LENGTH: 105
<212> TYPE: DNA
<213> ORGANISM: Artificial Sequence
<220> FEATURE:
<223> OTHER INFORMATION: Oligonucleotide for S66A/G67A/H83F/K85P/L86I
      mutations within EP4, EP5, and EP6

<400> SEQUENCE: 43
gtcaccgagt ccttctcgcc cgagccgatg atcggggtga aggcgatgac acggctgtcg      60
tcgggcttca ggtaatcctt gtccagggcg gcagccatgc cgtcg                     105

<210> SEQ ID NO 44
<211> LENGTH: 128
<212> TYPE: PRT
<213> ORGANISM: Pseudomonas aeruginosa

<400> SEQUENCE: 44

Ala Glu Cys Ser Val Asp Ile Gln Gly Asn Asp Gln Met Gln Phe Asn
1               5                   10                  15

Thr Asn Ala Ile Thr Val Asp Lys Ser Cys Lys Gln Phe Thr Val Asn
            20                  25                  30

Leu Ser His Pro Gly Asn Leu Pro Lys Asn Val Met Gly His Asn Trp
        35                  40                  45

Val Leu Ser Thr Ala Ala Asp Met Gln Gly Val Val Thr Asp Gly Met
    50                  55                  60

Ala Ser Gly Leu Asp Lys Asp Tyr Leu Lys Pro Asp Asp Ser Arg Val
65                  70                  75                  80

Ile Ala His Thr Lys Leu Ile Gly Ser Gly Glu Lys Asp Ser Val Thr
                85                  90                  95

Phe Asp Val Ser Lys Leu Lys Glu Gly Glu Gln Tyr Met Phe Phe Cys
            100                 105                 110

Thr Phe Pro Gly His Ser Ala Leu Met Lys Gly Thr Leu Thr Leu Lys
        115                 120                 125

<210> SEQ ID NO 45
<211> LENGTH: 128
<212> TYPE: PRT
<213> ORGANISM: Artificial Sequence
<220> FEATURE:
<223> OTHER INFORMATION: chimeric azurin mutant S1

<400> SEQUENCE: 45

Ala Glu Cys Ser Val Asp Ile Gln Gly Asn Asp Gln Met Gln Phe Asn
1               5                   10                  15

```
Thr Asn Ala Ile Gln Val Asp Lys Ser Cys Lys Gln Phe Thr Val Asn
            20                  25                  30

Leu Ser His Pro Gly Asn Leu Pro Lys Asn Val Met Gly His Asn Trp
        35                  40                  45

Val Leu Ser Thr Ala Ala Asp Met Gln Gly Val Val Thr Asp Gly Met
    50                  55                  60

Ala Ser Gly Leu Asp Lys Asp Tyr Leu Lys Pro Asp Asp Ser Arg Val
65                  70                  75                  80

Ile Ala His Thr Lys Leu Ile Gly Ser Gly Glu Lys Asp Ser Val Thr
                85                  90                  95

Phe Asp Val Ser Lys Leu Lys Glu Gly Glu Gln Tyr Met Phe Phe Cys
            100                 105                 110

Thr Phe Pro Gly His Ser Ala Leu Met Lys Gly Thr Leu Thr Leu Lys
        115                 120                 125

<210> SEQ ID NO 46
<211> LENGTH: 128
<212> TYPE: PRT
<213> ORGANISM: Artificial Sequence
<220> FEATURE:
<223> OTHER INFORMATION: chimeric azurin mutant S2

<400> SEQUENCE: 46

Ala Glu Cys Ser Val Asp Ile Gln Gly Asn Asp Gln Met Gln Phe Asn
1               5                   10                  15

Thr Asn Ala Ile Gln Val Asp Lys Ser Cys Lys Gln Phe Thr Val Asn
            20                  25                  30

Leu Ser His Pro Gly Asn Leu Pro Lys Asn Val Met Gly His Asn Trp
        35                  40                  45

Val Leu Ser Thr Ala Ala Asp Met Gln Gly Val Val Thr Asp Gly Met
    50                  55                  60

Ala Ser Gly Leu Asp Lys Asp Tyr Leu Lys Pro Asp Asp Ser Arg Val
65                  70                  75                  80

Ile Ala His Thr Lys Leu Ile Gly Ser Gly Glu Lys Asp Ser Val Thr
                85                  90                  95

Phe Asp Val Ser Lys Leu Lys Glu Gly Glu Gln Tyr Met Phe Phe Cys
            100                 105                 110

Thr Phe Pro Gly His Ser Ala Leu Met Lys Gly Thr Leu Lys Leu Lys
        115                 120                 125

<210> SEQ ID NO 47
<211> LENGTH: 128
<212> TYPE: PRT
<213> ORGANISM: Artificial Sequence
<220> FEATURE:
<223> OTHER INFORMATION: chimeric azurin mutant S3

<400> SEQUENCE: 47

Ala Glu Cys Ser Val Asp Ile Gln Gly Asn Asp Gln Met Gln Phe Asn
1               5                   10                  15

Thr Asn Ala Ile Gln Val Asp Lys Ser Cys Lys Gln Phe Thr Val Asn
            20                  25                  30

Leu Ser His Pro Gly Asn Leu Pro Lys Asn Val Met Gly His Asn Trp
        35                  40                  45

Val Leu Ser Lys Ser Ala Asp Met Gln Gly Val Val Thr Asp Gly Met
    50                  55                  60

Ala Ser Gly Leu Asp Lys Asp Tyr Leu Lys Pro Asp Asp Ser Arg Val
```

```
                65                  70                  75                  80
Ile Ala His Thr Lys Leu Ile Gly Ser Gly Glu Lys Asp Ser Val Thr
                85                  90                  95

Phe Asp Val Ser Lys Leu Lys Glu Gly Glu Gln Tyr Met Phe Phe Cys
            100                 105                 110

Thr Phe Pro Gly His Ser Ala Leu Met Lys Gly Thr Leu Lys Leu Lys
            115                 120                 125

<210> SEQ ID NO 48
<211> LENGTH: 128
<212> TYPE: PRT
<213> ORGANISM: Artificial Sequence
<220> FEATURE:
<223> OTHER INFORMATION: chimeric azurin mutant S3S5

<400> SEQUENCE: 48

Ala Glu Cys Ser Val Asp Ile Gln Gly Asn Asp Gln Met Gln Phe Asn
1               5                   10                  15

Thr Asn Ala Ile Gln Val Asp Lys Ser Cys Lys Gln Phe Thr Val Asn
                20                  25                  30

Leu Ser His Pro Gly Asn Leu Pro Lys Asn Val Met Gly His Asn Trp
            35                  40                  45

Val Leu Ser Lys Ser Ala Asp Met Gln Gly Val Ala Thr Asp Gly Met
    50                  55                  60

Ala Ala Ala Leu Asp Lys Asp Tyr Leu Lys Pro Asp Asp Ser Arg Val
65                  70                  75                  80

Ile Ala Phe Thr Pro Ile Ile Gly Ser Gly Glu Lys Asp Ser Val Thr
                85                  90                  95

Phe Asp Val Ser Lys Leu Lys Glu Gly Glu Gln Tyr Met Phe Phe Cys
            100                 105                 110

Thr Phe Pro Gly His Ser Ala Leu Met Lys Gly Thr Leu Lys Leu Lys
            115                 120                 125

<210> SEQ ID NO 49
<211> LENGTH: 128
<212> TYPE: PRT
<213> ORGANISM: Artificial Sequence
<220> FEATURE:
<223> OTHER INFORMATION: chimeric azurin mutant S3S5S4S6

<400> SEQUENCE: 49

Ala Glu Cys Ser Val Asp Ile Gln Gly Asn Asp Gln Met Gln Phe Asn
1               5                   10                  15

Thr Asn Ala Ile Gln Val Asp Lys Ser Cys Lys Gln Phe Thr Val Asn
                20                  25                  30

Leu Ser His Pro Gly Asn Leu Pro Lys Asn Val Met Gly His Asn Trp
            35                  40                  45

Val Leu Ser Lys Ser Ala Asp Met Gln Pro Ile Ala Thr Asp Gly Met
    50                  55                  60

Ala Ala Ala Leu Asp Lys Asp Tyr Leu Lys Pro Asp Asp Ser Arg Val
65                  70                  75                  80

Ile Ala Phe Thr Pro Ile Ile Gly Ser Gly Glu Lys Asp Ser Val Thr
                85                  90                  95

Phe Asp Val Ser Lys Leu Lys Glu Gly Glu Gln Tyr Met Phe Phe Cys
            100                 105                 110

Thr Phe Pro Gly His Ser Ala Leu Met Lys Gly Thr Leu Lys Leu Lys
            115                 120                 125
```

<210> SEQ ID NO 50
<211> LENGTH: 128
<212> TYPE: PRT
<213> ORGANISM: Artificial Sequence
<220> FEATURE:
<223> OTHER INFORMATION: chimeric azurin mutant S4

<400> SEQUENCE: 50

```
Ala Glu Cys Ser Val Asp Ile Gln Gly Asn Asp Gln Met Gln Phe Asn
1               5                   10                  15

Thr Asn Ala Ile Gln Val Asp Lys Ser Cys Lys Gln Phe Thr Val Asn
            20                  25                  30

Leu Ser His Pro Gly Asn Leu Pro Lys Asn Val Met Gly His Asn Trp
        35                  40                  45

Val Leu Ser Lys Ser Ala Asp Met Gln Met Ile Val Thr Asp Gly Met
    50                  55                  60

Ala Ser Gly Leu Asp Lys Asp Tyr Leu Lys Pro Asp Asp Ser Arg Val
65                  70                  75                  80

Ile Ala His Thr Lys Leu Ile Gly Ser Gly Glu Lys Asp Ser Val Thr
                85                  90                  95

Phe Asp Val Ser Lys Leu Lys Glu Gly Glu Gln Tyr Met Phe Phe Cys
            100                 105                 110

Thr Phe Pro Gly His Ser Ala Leu Met Lys Gly Thr Leu Lys Leu Lys
        115                 120                 125
```

<210> SEQ ID NO 51
<211> LENGTH: 128
<212> TYPE: PRT
<213> ORGANISM: Artificial Sequence
<220> FEATURE:
<223> OTHER INFORMATION: chimeric azurin mutant S6

<400> SEQUENCE: 51

```
Ala Glu Cys Ser Val Asp Ile Gln Gly Asn Asp Gln Met Gln Phe Asn
1               5                   10                  15

Thr Asn Ala Ile Gln Val Asp Lys Ser Cys Lys Gln Phe Thr Val Asn
            20                  25                  30

Leu Ser His Pro Gly Asn Leu Pro Lys Asn Val Met Gly His Asn Trp
        35                  40                  45

Val Leu Ser Lys Ser Ala Asp Met Gln Pro Ile Ala Thr Asp Gly Met
    50                  55                  60

Ala Ser Gly Leu Asp Lys Asp Tyr Leu Lys Pro Asp Asp Ser Arg Val
65                  70                  75                  80

Ile Ala His Thr Lys Leu Ile Gly Ser Gly Glu Lys Asp Ser Val Thr
                85                  90                  95

Phe Asp Val Ser Lys Leu Lys Glu Gly Glu Gln Tyr Met Phe Phe Cys
            100                 105                 110

Thr Phe Pro Gly His Ser Ala Leu Met Lys Gly Thr Leu Lys Leu Lys
        115                 120                 125
```

<210> SEQ ID NO 52
<211> LENGTH: 128
<212> TYPE: PRT
<213> ORGANISM: Artificial Sequence
<220> FEATURE:
<223> OTHER INFORMATION: chimeric azurin mutant wtS5

<400> SEQUENCE: 52

```
Ala Glu Cys Ser Val Asp Ile Gln Gly Asn Asp Gln Met Gln Phe Asn
```

```
1               5                   10                  15
Thr Asn Ala Ile Thr Val Asp Lys Ser Cys Lys Gln Phe Thr Val Asn
            20                  25                  30

Leu Ser His Pro Gly Asn Leu Pro Lys Asn Val Met Gly His Asn Trp
            35                  40                  45

Val Leu Ser Thr Ala Ala Asp Met Gln Gly Val Val Thr Asp Gly Met
        50                  55                  60

Ala Ala Ala Leu Asp Lys Asp Tyr Leu Lys Pro Asp Asp Ser Arg Val
65                  70                  75                  80

Ile Ala Phe Thr Pro Ile Ile Gly Ser Gly Glu Lys Asp Ser Val Thr
            85                  90                  95

Phe Asp Val Ser Lys Leu Lys Glu Gly Glu Gln Tyr Met Phe Phe Cys
                100                 105                 110

Thr Phe Pro Gly His Ser Ala Leu Met Lys Gly Thr Leu Thr Leu Lys
            115                 120                 125

<210> SEQ ID NO 53
<211> LENGTH: 128
<212> TYPE: PRT
<213> ORGANISM: Artificial Sequence
<220> FEATURE:
<223> OTHER INFORMATION: chimeric azurin mutant wtS5S4S6

<400> SEQUENCE: 53

Ala Glu Cys Ser Val Asp Ile Gln Gly Asn Asp Gln Met Gln Phe Asn
1               5                   10                  15

Thr Asn Ala Ile Thr Val Asp Lys Ser Cys Lys Gln Phe Thr Val Asn
            20                  25                  30

Leu Ser His Pro Gly Asn Leu Pro Lys Asn Val Met Gly His Asn Trp
            35                  40                  45

Val Leu Ser Thr Ala Ala Asp Met Gln Pro Ile Ala Thr Asp Gly Met
        50                  55                  60

Ala Ala Ala Leu Asp Lys Asp Tyr Leu Lys Pro Asp Asp Ser Arg Val
65                  70                  75                  80

Ile Ala Phe Thr Pro Ile Ile Gly Ser Gly Glu Lys Asp Ser Val Thr
            85                  90                  95

Phe Asp Val Ser Lys Leu Lys Glu Gly Glu Gln Tyr Met Phe Phe Cys
                100                 105                 110

Thr Phe Pro Gly His Ser Ala Leu Met Lys Gly Thr Leu Thr Leu Lys
            115                 120                 125
```